(12) United States Patent
Zhang et al.

(10) Patent No.: US 10,738,314 B2
(45) Date of Patent: Aug. 11, 2020

(54) IRRE PROTEIN FUNCTIONAL DOMAIN FOR IMPROVING ANTI-OXIDATION CAPABILITY OF CELL AND APPLICATION THEREOF

(71) Applicant: BIOTECHNOLOGY RESEARCH INSTITUTE, CHINESE ACADEMY OF AGRICULTURAL SCIENCES, Beijing (CN)

(72) Inventors: Wei Zhang, Beijing (CN); Zhengfu Zhou, Beijing (CN); Ming Chen, Beijing (CN); Min Lin, Beijing (CN)

(73) Assignee: BIOTECHNOLOGY RESEARCH INSTITUTE, CHINESE ACADEMY OF AGRICULTURAL SCIENCES, Beijing (CN)

( * ) Notice: Subject to any disclaimer, the term of this patent is extended or adjusted under 35 U.S.C. 154(b) by 0 days.

(21) Appl. No.: 15/553,599

(22) PCT Filed: May 9, 2016

(86) PCT No.: PCT/CN2016/081403
§ 371 (c)(1),
(2) Date: Aug. 25, 2017

(87) PCT Pub. No.: WO2016/180300
PCT Pub. Date: Nov. 17, 2016

(65) Prior Publication Data
US 2018/0163215 A1    Jun. 14, 2018

(30) Foreign Application Priority Data
May 11, 2015   (CN) ............. 2015 1 0236790

(51) Int. Cl.
  *C12N 15/70*    (2006.01)
  *C07K 14/195*   (2006.01)
  *C12Q 1/686*    (2018.01)
(52) U.S. Cl.
  CPC ............ *C12N 15/70* (2013.01); *C07K 14/195* (2013.01); *C12Q 1/686* (2013.01)

(58) Field of Classification Search
None
See application file for complete search history.

(56) References Cited

FOREIGN PATENT DOCUMENTS

| CN | 101671679 A | * | 3/2010 |
| CN | 202443018 U | | 9/2012 |
| CN | 104830873 A | | 8/2015 |
| EP | 2917365 A1 | | 9/2015 |

OTHER PUBLICATIONS

Chen et al., Laboratory-Evolved Mutants of an Exogenous Global Regulator, IrrE from Deinococcus radiodurans, Enhance Stress Tolerances of *Escherichia coli*; PLoS One, vol. 6, No. 1, e16288, pp. 1-11, 2011 (Year: 2011).*
Misra et al., Physiological and molecular basis of extreme radioresistance in Deinococcus radiodurans; Current Science, vol. 104, No. 2, pp. 194-205, 2013 (Year: 2013).*
CN-101671679-A Machine translation from Google Patents, accessed Mar. 11, 2019 (Year: 2019).*
Sambrook et al, "Molecular Cloning: A Laboratory Manual", New York: Cold Spring Harbor Laboratory Press,1989.
Dulermo.R.et al."Crystal Structure of the IrrE Protein, a Central Regulator of DNA Damage Repair in Deinococcaceae", Journal of the Molecular Biology, vol. 386, No. 3, Feb. 27, 2009,ISSN:0022-0283, see, p. 709,paragraph 2.
Chen Zhen et al,"Research Progress of the Global Regulator IrrE in Deinococcus Radiodurans", Current Biotechnology, vol. 3, No. 3, Mar. 31, 2013, ISSN:2095-2341,see p. 182,paragraph 2.
"GenBank accession No. ABF44698.1" Genbank, Jan. 28, 2014. see sequence.

* cited by examiner

*Primary Examiner* — Nancy A Treptow
(74) *Attorney, Agent, or Firm* — Bayramoglu Law Offices LLC

(57) ABSTRACT

Provided is an amino acid optimization of a functional motif on an IrrE protein of a *Deinococcus geothermalis* strain and homologous proteins thereof obtained by site mutation, wherein a second-site or fifth-site alanine in a functional domain motif 154LAELAR159 is mutated. into serine.

3 Claims, 5 Drawing Sheets
Specification includes a Sequence Listing.

SEQUENCE LISTING

<160> NUMBER OF SEQ ID NOS: 58

<210> SEQ ID NO 1
<211> LENGTH: 870
<212> TYPE: DNA
<213> ORGANISM: Deinococcus geothermalis

<400> SEQUENCE: 1

```
gtgacgcagg gccagacccc acccgaggag ctttccgccg accccctcgcc ggagactgga      60 gcgctggccc cggccaaggc gcgtatgcgg gaactggcga ctgcctacgc tcgccgtttg     120
ccggggctgg atacccacag cctgatgagc gggctggacg cgaccctcac ctttatgccg     180
```

```
atgggtgacc gtgacggagc ctatgacccc gagcaccgcg tggtgctgat caacagtcgg    240
gtacgcccgg aacgccagcg cttcacactg gcccacgaga tcagccatgc cctcctgctg    300
ggcgacgacg acttgctcag cgatctgcac gacgcctacg agggagagcg gttggagcag    360
gtcatagaga cactttgcaa tgtgggggca gcagcgatcc tgatgcccga gaccctgatt    420
gacgagctgc tcgcgcgctt tgggccgagt gggcgtgcgc tggctgagct ggcgcggcgg    480
gcagacgtga gtgccagcag tgccctctat gccctggcgg agcgaacctc agtgccggtg    540
ctgtacgcgg tgtgcgcggt cagccggctg gaagcagaat ccggagagga acggctcccc    600
gaaaaggcgc ttactgttcg ggccagtgcg ggatcacccg gcgtgaagta cagcctgcgc    660
cccggcacgc tcatcccaga tgaccacccg gtcgccgttg cgctggaaac gcggctgccc    720
atcacccagg agagttacgt gcccttccgt tcgggcggc ggatgcccgc ctatgtcgac    780 gccttcctg agcgtcagcg ggtgctggtg agttttgccc tcttgcccaa agcgacgaag    840
ggaggcgagc aggatgagtc gggtgtctga                                    870
```

```
<210> SEQ ID NO 2
<211> LENGTH: 289
<212> TYPE: PRT
<213> ORGANISM: Deinococcus geothermalis

<400> SEQUENCE: 2

Val Thr Gln Gly Gln Thr Pro Pro Glu Glu Leu Ser Ala Asp Pro Ser
1               5                   10                  15

Pro Glu Thr Gly Ala Leu Ala Pro Ala Lys Ala Arg Met Arg Glu Leu
            20                  25                  30

Ala Thr Ala Tyr Ala Arg Arg Leu Pro Gly Leu Asp Thr His Ser Leu
        35                  40                  45

Met Ser Gly Leu Asp Ala Thr Leu Thr Phe Met Pro Met Gly Asp Arg
    50                  55                  60

Asp Gly Ala Tyr Asp Pro Glu His Arg Val Val Leu Ile Asn Ser Arg
65                  70                  75                  80

Val Arg Pro Glu Arg Gln Arg Phe Thr Leu Ala His Glu Ile Ser His
                85                  90                  95

Ala Leu Leu Leu Gly Asp Asp Asp Leu Leu Ser Asp Leu His Asp Ala
            100                 105                 110

Tyr Glu Gly Glu Arg Leu Glu Gln Val Ile Glu Thr Leu Cys Asn Val
        115                 120                 125

Gly Ala Ala Ala Ile Leu Met Pro Glu Thr Leu Ile Asp Glu Leu Leu
    130                 135                 140

Ala Arg Phe Gly Pro Ser Gly Arg Ala Leu Ala Glu Leu Ala Arg Arg
145                 150                 155                 160

Ala Asp Val Ser Ala Ser Ser Ala Leu Tyr Ala Leu Ala Glu Arg Thr
                165                 170                 175

Ser Val Pro Val Leu Tyr Ala Val Cys Ala Val Ser Arg Leu Glu Ala
            180                 185                 190

Glu Ser Gly Glu Glu Arg Leu Pro Glu Lys Ala Leu Thr Val Arg Ala
        195                 200                 205

Ser Ala Gly Ser Pro Gly Val Lys Tyr Ser Leu Arg Pro Gly Thr Leu
    210                 215                 220

Ile Pro Asp Asp His Pro Val Ala Val Ala Leu Glu Thr Arg Leu Pro
225                 230                 235                 240

Ile Thr Gln Glu Ser Tyr Val Pro Phe Arg Ser Gly Arg Arg Met Pro
                245                 250                 255
```

```
Ala Tyr Val Asp Ala Phe Pro Glu Arg Gln Arg Val Leu Val Ser Phe
            260                 265                 270

Ala Leu Leu Pro Lys Ala Thr Lys Gly Gly Glu Gln Asp Glu Ser Gly
        275                 280                 285

Val

<210> SEQ ID NO 3
<211> LENGTH: 6
<212> TYPE: PRT
<213> ORGANISM: Deinococcus geothermalis

<400> SEQUENCE: 3

Leu Ala Glu Leu Ala Arg
1               5

<210> SEQ ID NO 4
<211> LENGTH: 6
<212> TYPE: PRT
<213> ORGANISM: Artificial sequence
<220> FEATURE:
<223> OTHER INFORMATION: artificial modification on functional domain
      motif in SEQ ID NO.3

<400> SEQUENCE: 4

Leu Ser Glu Leu Ala Arg
1               5

<210> SEQ ID NO 5
<211> LENGTH: 6
<212> TYPE: PRT
<213> ORGANISM: Artificial sequence
<220> FEATURE:
<223> OTHER INFORMATION: artificial modification on functional domain
      motif in SEQ ID NO.3

<400> SEQUENCE: 5

Leu Ala Glu Leu Ser Arg
1               5

<210> SEQ ID NO 6
<211> LENGTH: 328
<212> TYPE: PRT
<213> ORGANISM: Deinococcus radiodurans

<400> SEQUENCE: 6

Val Pro Ser Ala Asn Val Ser Pro Pro Cys Pro Ser Gly Val Arg Gly
1               5                   10                  15

Gly Gly Met Gly Pro Lys Ala Lys Ala Glu Ala Ser Lys Pro His Pro
            20                  25                  30

Gln Ile Pro Val Lys Leu Pro Phe Val Thr Ala Pro Asp Ala Leu Ala
        35                  40                  45

Ala Ala Lys Ala Arg Met Arg Asp Leu Ala Ala Tyr Val Ala Ala
    50                  55                  60

Leu Pro Gly Arg Asp Thr His Ser Leu Met Ala Gly Val Pro Gly Val
65                  70                  75                  80

Asp Leu Lys Phe Met Pro Leu Gly Trp Arg Asp Gly Ala Phe Asp Pro
                85                  90                  95

Glu His Asn Val Ile Leu Ile Asn Ser Ala Ala Arg Pro Glu Arg Gln
            100                 105                 110

Arg Phe Thr Leu Ala His Glu Ile Gly His Ala Ile Leu Leu Gly Asp
        115                 120                 125
```

```
Asp Asp Leu Leu Ser Asp Ile His Asp Ala Tyr Glu Gly Glu Arg Leu
            130                 135                 140

Glu Gln Val Ile Glu Thr Leu Cys Asn Val Ala Ala Ala Ile Leu
145                 150                 155                 160

Met Pro Glu Pro Val Ile Ala Glu Met Leu Glu Arg Phe Gly Pro Thr
                    165                 170                 175

Gly Arg Ala Leu Ala Glu Leu Ala Lys Arg Ala Glu Val Ser Ala Ser
                180                 185                 190

Ser Ala Leu Tyr Ala Leu Thr Glu Gln Thr Pro Val Pro Val Ile Tyr
                195                 200                 205

Ala Val Cys Ala Pro Gly Lys Pro Pro Arg Glu Gln Ala Ala Ser Asp
            210                 215                 220

Glu Asp Ala Gly Pro Ser Thr Glu Lys Val Leu Thr Val Arg Ala Ser
225                 230                 235                 240

Ser Ser Thr Arg Gly Val Lys Tyr Thr Leu Ala Ser Gly Thr Pro Val
                245                 250                 255

Pro Ala Asp His Pro Ala Ala Leu Ala Leu Ala Thr Gly Met Glu Val
                260                 265                 270

Arg Glu Glu Ser Tyr Val Pro Phe Arg Ser Gly Arg Lys Met Lys Ala
            275                 280                 285

Glu Val Asp Ala Tyr Pro Ser Arg Gly Ile Val Ala Val Ser Phe Glu
290                 295                 300

Phe Asp Pro Ala Arg Leu Gly Arg Lys Asp Ser Gln Ala Asp Arg
305                 310                 315                 320

Asp Glu Pro Gln Asp Ala Ala Gln
                325

<210> SEQ ID NO 7
<211> LENGTH: 256
<212> TYPE: PRT
<213> ORGANISM: Deinococcus gobiensis

<400> SEQUENCE: 7

Met Arg Glu Leu Ala Ala Tyr Ala Ala Arg Val Pro Ser Leu Asp
1               5                   10                  15

Ala His Gly Leu Met Asp Gly Leu Asp Gly Val Gln Leu Arg Phe Met
                20                  25                  30

Pro Met Gly Gln Arg Asp Gly Ala Tyr Asp Pro Glu His His Val Ile
                35                  40                  45

Leu Ile Asn Ser Gln Val Arg Pro Glu Arg Gln Arg Phe Thr Leu Ala
        50                  55                  60

His Glu Ile Ser His Ala Leu Leu Gly Asp Asp Asp Leu Leu Ser
65                  70                  75                  80

Asp Leu His Asp Ser Phe Glu Gly Glu Arg Leu Glu Gln Val Ile Glu
                85                  90                  95

Thr Leu Cys Asn Val Gly Ala Ala Leu Leu Met Pro Asp Ala Leu
                100                 105                 110

Ile Ala Glu Leu Leu Glu Arg Phe Gly Ala Thr Gly Arg Ala Leu Ala
            115                 120                 125

Glu Leu Ser Arg Arg Ala Asp Val Ser Ala Ser Thr Ala Leu Tyr Ala
130                 135                 140

Leu Ala Glu Arg Thr Pro Gly Ala Val Leu Tyr Ala Val Cys Thr Arg
145                 150                 155                 160

Ser Arg Leu Glu Thr Glu Thr Asp Asp Glu Asp Gly Gly Ala Ala Ser
```

```
            165                 170                 175
Gly Thr Ala Leu Thr Val Arg Val Ser Gly Ser Ala Gly Met Lys
        180                 185                 190

Tyr Thr Leu Arg Pro Gly Thr Pro Ile Pro Ala Asp His Pro Val Gln
        195                 200                 205

Ala Ala Phe Glu Ser Asn Leu Pro Leu Thr Gly Pro Ser Tyr Val Pro
    210                 215                 220

Phe Arg Ser Gly Arg Lys Met Pro Ala Glu Val Asp Ala Phe Pro Val
225                 230                 235                 240

Arg Gly Arg Val Met Val Ser Phe Asp Leu Asn Gly Arg Gly Thr
                245                 250                 255

<210> SEQ ID NO 8
<211> LENGTH: 289
<212> TYPE: PRT
<213> ORGANISM: Artificial sequence
<220> FEATURE:
<223> OTHER INFORMATION: the modified amino acid sequence of Deinococcus
      geothermalis IrrE

<400> SEQUENCE: 8

Val Thr Gln Gly Gln Thr Pro Pro Glu Glu Leu Ser Ala Asp Pro Ser
1               5                   10                  15

Pro Glu Thr Gly Ala Leu Ala Pro Ala Lys Ala Arg Met Arg Glu Leu
            20                  25                  30

Ala Thr Ala Tyr Ala Arg Arg Leu Pro Gly Leu Asp Thr His Ser Leu
        35                  40                  45

Met Ser Gly Leu Asp Ala Thr Leu Thr Phe Met Pro Met Gly Asp Arg
    50                  55                  60

Asp Gly Ala Tyr Asp Pro Glu His Arg Val Val Leu Ile Asn Ser Arg
65                  70                  75                  80

Val Arg Pro Glu Arg Gln Arg Phe Thr Leu Ala His Glu Ile Ser His
                85                  90                  95

Ala Leu Leu Leu Gly Asp Asp Asp Leu Leu Ser Asp Leu His Asp Ala
            100                 105                 110

Tyr Glu Gly Glu Arg Leu Glu Gln Val Ile Glu Thr Leu Cys Asn Val
        115                 120                 125

Gly Ala Ala Ala Ile Leu Met Pro Glu Thr Leu Ile Asp Glu Leu Leu
    130                 135                 140

Ala Arg Phe Gly Pro Ser Gly Arg Ala Leu Ser Glu Leu Ala Arg Arg
145                 150                 155                 160

Ala Asp Val Ser Ala Ser Ser Ala Leu Tyr Ala Leu Ala Glu Arg Thr
                165                 170                 175

Ser Val Pro Val Leu Tyr Ala Val Cys Ala Val Ser Arg Leu Glu Ala
            180                 185                 190

Glu Ser Gly Glu Glu Arg Leu Pro Glu Lys Ala Leu Thr Val Arg Ala
        195                 200                 205

Ser Ala Gly Ser Pro Gly Val Lys Tyr Ser Leu Arg Pro Gly Thr Leu
    210                 215                 220

Ile Pro Asp Asp His Pro Val Ala Val Ala Leu Glu Thr Arg Leu Pro
225                 230                 235                 240

Ile Thr Gln Glu Ser Tyr Val Pro Phe Arg Ser Gly Arg Arg Met Pro
                245                 250                 255

Ala Tyr Val Asp Ala Phe Pro Glu Arg Gln Arg Val Leu Val Ser Phe
            260                 265                 270
```

```
Ala Leu Leu Pro Lys Ala Thr Lys Gly Gly Glu Gln Asp Glu Ser Gly
            275                 280                 285
Val

<210> SEQ ID NO 9
<211> LENGTH: 289
<212> TYPE: PRT
<213> ORGANISM: Artificial sequence
<220> FEATURE:
<223> OTHER INFORMATION: the modified amino acid sequence of Deinococcus
      geothermalis IrrE.

<400> SEQUENCE: 9

Val Thr Gln Gly Gln Thr Pro Pro Glu Glu Leu Ser Ala Asp Pro Ser
1               5                   10                  15

Pro Glu Thr Gly Ala Leu Ala Pro Ala Lys Ala Arg Met Arg Glu Leu
            20                  25                  30

Ala Thr Ala Tyr Ala Arg Arg Leu Pro Gly Leu Asp Thr His Ser Leu
        35                  40                  45

Met Ser Gly Leu Asp Ala Thr Leu Thr Phe Met Pro Met Gly Asp Arg
    50                  55                  60

Asp Gly Ala Tyr Asp Pro Glu His Arg Val Val Leu Ile Asn Ser Arg
65                  70                  75                  80

Val Arg Pro Glu Arg Gln Arg Phe Thr Leu Ala His Glu Ile Ser His
                85                  90                  95

Ala Leu Leu Leu Gly Asp Asp Leu Leu Ser Asp Leu His Asp Ala
            100                 105                 110

Tyr Glu Gly Glu Arg Leu Glu Gln Val Ile Glu Thr Leu Cys Asn Val
            115                 120                 125

Gly Ala Ala Ala Ile Leu Met Pro Glu Thr Leu Ile Asp Glu Leu Leu
        130                 135                 140

Ala Arg Phe Gly Pro Ser Gly Arg Ala Leu Ala Glu Leu Ser Arg Arg
145                 150                 155                 160

Ala Asp Val Ser Ala Ser Ser Ala Leu Tyr Ala Leu Ala Glu Arg Thr
                165                 170                 175

Ser Val Pro Val Leu Tyr Ala Val Cys Ala Val Ser Arg Leu Glu Ala
            180                 185                 190

Glu Ser Gly Glu Glu Arg Leu Pro Glu Lys Ala Leu Thr Val Arg Ala
        195                 200                 205

Ser Ala Gly Ser Pro Gly Val Lys Tyr Ser Leu Arg Pro Gly Thr Leu
    210                 215                 220

Ile Pro Asp Asp His Pro Val Ala Val Ala Leu Glu Thr Arg Leu Pro
225                 230                 235                 240

Ile Thr Gln Glu Ser Tyr Val Pro Phe Arg Ser Gly Arg Arg Met Pro
                245                 250                 255

Ala Tyr Val Asp Ala Phe Pro Glu Arg Gln Arg Val Leu Val Ser Phe
            260                 265                 270

Ala Leu Leu Pro Lys Ala Thr Lys Gly Gly Glu Gln Asp Glu Ser Gly
        275                 280                 285

Val

<210> SEQ ID NO 10
<211> LENGTH: 289
<212> TYPE: PRT
<213> ORGANISM: Artificial sequence
<220> FEATURE:
<223> OTHER INFORMATION: the modified amino acid sequence of Deinococcus
``` geothermalis IrrE

<400> SEQUENCE: 10

Val Thr Gln Gly Gln Thr Pro Pro Glu Glu Leu Ser Ala Asp Pro Ser
1               5                   10                  15

Pro Glu Thr Gly Ala Leu Ala Pro Ala Lys Ala Arg Met Arg Glu Leu
            20                  25                  30

Ala Thr Ala Tyr Ala Arg Arg Leu Pro Gly Leu Asp Thr His Ser Leu
        35                  40                  45

Met Ser Gly Leu Asp Ala Thr Leu Thr Phe Met Pro Met Gly Asp Arg
    50                  55                  60

Asp Gly Ala Tyr Asp Pro Glu His Arg Val Val Leu Ile Asn Ser Arg
65                  70                  75                  80

Val Arg Pro Glu Arg Gln Arg Phe Thr Leu Ala His Glu Ile Ser His
                85                  90                  95

Ala Leu Leu Leu Gly Asp Asp Leu Leu Ser Asp Leu His Asp Ala
            100                 105                 110

Tyr Glu Gly Glu Arg Leu Glu Gln Val Ile Glu Thr Leu Cys Asn Val
            115                 120                 125

Gly Ala Ala Ile Leu Met Pro Glu Thr Leu Ile Asp Glu Leu Leu
130                 135                 140

Ala Arg Phe Gly Pro Ser Gly Arg Ala Leu Ser Glu Leu Ser Arg Arg
145                 150                 155                 160

Ala Asp Val Ser Ala Ser Ser Ala Leu Tyr Ala Leu Ala Glu Arg Thr
                165                 170                 175

Ser Val Pro Val Leu Tyr Ala Val Cys Ala Val Ser Arg Leu Glu Ala
            180                 185                 190

Glu Ser Gly Glu Glu Arg Leu Pro Glu Lys Ala Leu Thr Val Arg Ala
            195                 200                 205

Ser Ala Gly Ser Pro Gly Val Lys Tyr Ser Leu Arg Pro Gly Thr Leu
    210                 215                 220

Ile Pro Asp Asp His Pro Val Ala Val Ala Leu Glu Thr Arg Leu Pro
225                 230                 235                 240

Ile Thr Gln Glu Ser Tyr Val Pro Phe Arg Ser Gly Arg Met Pro
                245                 250                 255

Ala Tyr Val Asp Ala Phe Pro Glu Arg Gln Arg Val Leu Val Ser Phe
            260                 265                 270

Ala Leu Leu Pro Lys Ala Thr Lys Gly Gly Glu Gln Asp Glu Ser Gly
        275                 280                 285

Val

<210> SEQ ID NO 11
<211> LENGTH: 262
<212> TYPE: PRT
<213> ORGANISM: Deinococcus apachensis

<400> SEQUENCE: 11

Met Arg Glu Leu Ala Ser Ala Tyr Val Arg Gly Leu Pro Gly Leu Asp
1               5                   10                  15

Thr His Ser Leu Met Ser Gly Leu Asp Ala Thr Leu Thr Phe Met Pro
            20                  25                  30

Met Gly Asp Arg Asp Gly Ala Tyr Asp Pro Glu His Arg Val Val Leu
        35                  40                  45

Ile Asn Ser Arg Val Arg Pro Glu Arg Gln Arg Phe Thr Leu Ala His
    50                  55                  60

```
Glu Ile Ser His Ala Leu Leu Gly Asp Asp Leu Leu Ser Asp
 65                  70                  75                  80

Leu His Asp Ala Tyr Glu Gly Glu Arg Leu Glu Gln Val Ile Glu Thr
                 85                  90                  95

Leu Cys Asn Val Gly Ala Ala Ile Leu Met Pro Asp Ala Leu Ile
            100                 105                 110

Asp Glu Leu Leu Ala Arg Phe Gly Pro Ser Gly Arg Ala Leu Ala Glu
                115                 120                 125

Leu Ala Arg Arg Ala Asp Val Ser Ala Ser Ala Leu Tyr Ala Leu
    130                 135                 140

Ala Glu Arg Thr Ala Ala Pro Val Leu Tyr Ala Val Cys Ala Val Ala
145                 150                 155                 160

Arg Leu Glu Ala Glu Pro Gly Asp Glu Arg Pro Thr Gly Lys Ala
                165                 170                 175

Leu Thr Val Arg Ala Ser Gly Gly Ala Pro Ser Val Lys Tyr Ser Leu
                180                 185                 190

Arg Pro Gly Thr Leu Ile Pro Ala Glu His Pro Val Ala Val Ala Leu
                195                 200                 205

Glu Thr His Leu Pro Ile Ala Gln Glu Ser Tyr Val Pro Phe Arg Ser
    210                 215                 220

Gly Arg Arg Met Pro Ala Tyr Val Asp Ala Phe Pro Glu Arg Gln Arg
225                 230                 235                 240

Val Met Val Ser Phe Thr Leu Thr Pro Arg Pro Thr Lys Gly Gly Glu
                245                 250                 255

Ser Asp Glu Pro Ala Gly
            260

<210> SEQ ID NO 12
<211> LENGTH: 288
<212> TYPE: PRT
<213> ORGANISM: Deinococcus phoenicis

<400> SEQUENCE: 12

Met Thr Gln Gly Arg Thr Pro Thr Glu Pro Ile Ser Ala Asp Ala Ser
  1               5                  10                  15

Pro Asp Ala Gly Ala Leu Ala Pro Ala Lys Ala Arg Met Arg Glu Leu
                 20                  25                  30

Ala Ala Ala Tyr Val Gln Gly Leu Pro Gly Leu Asp Thr His Ser Leu
             35                  40                  45

Met Ser Gly Leu Asp Ala Thr Leu Thr Phe Leu Pro Met Gly Asp Arg
 50                  55                  60

Asp Gly Ala Tyr Asp Pro Glu His Arg Val Val Leu Ile Asn Ser Arg
 65                  70                  75                  80

Val Arg Pro Glu Arg Gln Arg Phe Thr Leu Ala His Glu Ile Ser His
                 85                  90                  95

Ala Leu Leu Leu Gly Asp Asp Leu Leu Ser Asp Leu His Asp Ala
            100                 105                 110

Tyr Glu Gly Glu Arg Leu Glu Gln Val Ile Glu Thr Leu Cys Asn Ile
                115                 120                 125

Gly Ala Ala Ile Leu Met Pro Glu Ala Leu Ile Asp Glu Val Val
    130                 135                 140

Ser Arg Phe Gly Pro Ser Gly Arg Ala Leu Ala Glu Leu Ala Arg Arg
145                 150                 155                 160

Ala Asp Val Ser Ala Ser Ser Ala Leu Tyr Ala Leu Ala Glu Arg Thr
```

```
            165                 170                 175
Thr Ala Pro Val Leu Tyr Ala Val Cys Ala Val Thr Arg Leu Ala Glu
        180                 185                 190

Pro Gly Glu Arg Pro Ser Asp Lys Ala Leu Thr Val Arg Ala Ser
        195                 200                 205

Gly Gly Ala Pro Gly Val Lys Tyr Ser Leu Arg Pro Gly Thr Arg Ile
        210                 215                 220

Pro Asp His Pro Val Ala Val Ala Leu Glu Thr His Leu Pro Met
225             230                 235                 240

Thr Gln Glu Ser Tyr Val Pro Phe Arg Ser Gly Arg Met Pro Ala
            245                 250                 255

Tyr Val Asp Ala Phe Pro Glu Arg Gln Arg Val Leu Val Ser Phe Ala
            260                 265                 270

Leu Met Pro Arg Ala Ala Arg Gly Ser Glu Asp Glu Pro Val Thr
            275                 280                 285

<210> SEQ ID NO 13
<211> LENGTH: 260
<212> TYPE: PRT
<213> ORGANISM: Deinococcus phoenicis

<400> SEQUENCE: 13

Met Arg Glu Leu Ala Ala Ala Tyr Val Gln Gly Leu Pro Gly Leu Asp
1               5                   10                  15

Thr His Ser Leu Met Ser Gly Leu Asp Ala Thr Leu Thr Phe Leu Pro
            20                  25                  30

Met Gly Asp Arg Asp Gly Ala Tyr Asp Pro Glu His Arg Val Val Leu
        35                  40                  45

Ile Asn Ser Arg Val Arg Pro Glu Arg Gln Arg Phe Thr Leu Ala His
    50                  55                  60

Glu Ile Ser His Ala Leu Leu Leu Gly Asp Asp Leu Leu Ser Asp
65                  70                  75                  80

Leu His Asp Ala Tyr Glu Gly Glu Arg Leu Glu Gln Val Ile Glu Thr
                85                  90                  95

Leu Cys Asn Ile Gly Ala Ala Ile Leu Met Pro Glu Ala Leu Ile
            100                 105                 110

Asp Glu Val Val Ser Arg Phe Gly Pro Ser Gly Arg Ala Leu Ala Glu
        115                 120                 125

Leu Ala Arg Arg Ala Asp Val Ser Ala Ser Ser Ala Leu Tyr Ala Leu
130                 135                 140

Ala Glu Arg Thr Thr Ala Pro Val Leu Tyr Ala Val Cys Ala Val Thr
145                 150                 155                 160

Arg Leu Ala Glu Pro Gly Glu Arg Pro Ser Asp Lys Ala Leu Thr
            165                 170                 175

Val Arg Ala Ser Gly Gly Ala Pro Gly Val Lys Tyr Ser Leu Arg Pro
        180                 185                 190

Gly Thr Arg Ile Pro Asp Asp His Pro Val Ala Val Ala Leu Glu Thr
        195                 200                 205

His Leu Pro Met Thr Gln Glu Ser Tyr Val Pro Phe Arg Ser Gly Arg
    210                 215                 220

Arg Met Pro Ala Tyr Val Asp Ala Phe Pro Glu Arg Gln Arg Val Leu
225                 230                 235                 240

Val Ser Phe Ala Leu Met Pro Arg Ala Ala Arg Gly Ser Glu Asp Asp
                245                 250                 255
```

```
Glu Pro Val Thr
            260

<210> SEQ ID NO 14
<211> LENGTH: 262
<212> TYPE: PRT
<213> ORGANISM: Deinococcus sp.

<400> SEQUENCE: 14

Met Arg Glu Leu Ala Ala Tyr Ala Arg Arg Leu Pro Gly Leu Asp
1               5                   10                  15

Thr His Ser Leu Met Ser Gly Leu Asp Ala Thr Leu Lys Phe Met Pro
            20                  25                  30

Met Gly Asp Arg Asp Gly Ala Tyr Asp Pro Glu His Arg Val Val Leu
            35                  40                  45

Ile Asn Ser Gln Val Arg Pro Glu Arg Gln Arg Phe Thr Leu Ala His
    50                  55                  60

Glu Ile Ser His Ala Leu Leu Gly Asp Asp Leu Leu Ser Asp
65                  70                  75                  80

Leu His Asp Ala Phe Glu Gly Glu Arg Leu Glu Gln Val Ile Glu Thr
                85                  90                  95

Leu Cys Asn Val Gly Ala Ala Ala Leu Leu Met Pro Glu Ala Leu Val
                100                 105                 110

Asp Glu Val Met Ala Arg Phe Gly Pro Thr Gly Arg Ala Leu Ala Glu
            115                 120                 125

Leu Ser Arg Arg Ala Asp Val Ser Ala Ser Ala Leu Tyr Ala Leu
    130                 135                 140

Ala Glu Arg Thr Thr Ala Pro Val Leu Tyr Ala Val Cys Ala Leu Thr
145                 150                 155                 160

Arg Pro Glu Val Glu Gly Ser Asp Glu Ala Arg Pro Ala Glu Lys Val
                165                 170                 175

Leu Thr Val Arg Val Ser Gly Gly Ala Pro Gly Val Lys Tyr Ser Leu
            180                 185                 190

Arg Pro Gly Thr Val Ile Pro Asp Asp His Pro Val Ala Ala Leu
    195                 200                 205

Glu Thr His Leu Pro Ile Gly Gln Glu Ser Tyr Val Pro Phe Arg Ser
210                 215                 220

Gly Arg Arg Met Pro Ala Tyr Val Asp Ala Phe Pro Glu Arg Gln Arg
225                 230                 235                 240

Val Leu Val Ser Phe Ala Leu Arg Pro Arg Pro Ala Lys Gly Gly Glu
                245                 250                 255

Asp His Asp Pro Glu Ala
            260

<210> SEQ ID NO 15
<211> LENGTH: 256
<212> TYPE: PRT
<213> ORGANISM: Deinococcus murrayi

<400> SEQUENCE: 15

Met Arg Glu Leu Ala Ala Thr Tyr Ala Ser Gly Leu Pro Gly Arg Asp
1               5                   10                  15

Thr His Ser Leu Leu Ala Gly Leu Asp Ala Thr Leu Arg Phe Leu Pro
            20                  25                  30

Met Gly Glu Arg Asp Gly Ala Tyr Asp Pro Glu His Arg Val Val Leu
            35                  40                  45
```

```
Ile Asn Ser Arg Val Arg Pro Glu Arg Gln Arg Phe Thr Leu Ala His
 50                  55                  60

Glu Val Ser His Ala Leu Leu Ala Asp Asp Asp Leu Leu Ser Asp
 65                  70                  75                  80

Leu His Asp Ala Phe Glu Gly Glu Arg Leu Glu Gln Val Ile Glu Thr
                 85                  90                  95

Leu Cys Asn Val Gly Ala Ala Leu Leu Met Pro Asp Ala Leu Ile
                100                 105                 110

Asp Glu Val Leu Ala Arg His Gly Pro Ser Gly Gln Ala Leu Ala Asp
            115                 120                 125

Leu Ser Arg Arg Ala Glu Val Ser Ala Ser Ala Leu Tyr Ala Leu
130                 135                 140

Ala Gly Arg Thr Ser Ala Pro Val Leu Tyr Ala Val Cys Ala Val Ser
145                 150                 155                 160

Arg Leu Glu Thr Glu Ala Glu Thr Pro Pro Gly Lys Gly Leu Thr
                165                 170                 175

Val Arg Ala Ser Ser Gly Ala Pro Gly Val Arg Tyr Ser Leu Arg Pro
            180                 185                 190

Gly Thr Pro Ile Pro Asp Asp His Pro Val Ala Leu Ser Leu Ala Thr
            195                 200                 205

His Leu Pro Leu Ala Gln Glu Ser Tyr Val Pro Phe Arg Ser Gly Arg
210                 215                 220

Arg Met Pro Ala Tyr Val Asp Ala Phe Pro Glu Arg Gln Arg Val Leu
225                 230                 235                 240

Val Ser Phe Ala Leu Gly Gln Arg Gly Arg Val Gly Glu Asp Gly Glu
                245                 250                 255

<210> SEQ ID NO 16
<211> LENGTH: 256
<212> TYPE: PRT
<213> ORGANISM: Deinococcus sp.

<400> SEQUENCE: 16

Met Arg Glu Leu Ala Ala Thr Tyr Ala Ser Gly Leu Pro Gly Arg Asp
 1               5                  10                  15

Thr His Ser Leu Leu Ala Gly Leu Asp Ala Thr Leu Arg Phe Leu Pro
                 20                  25                  30

Met Gly Glu Arg Asp Gly Ala Tyr Asp Pro Glu His Arg Val Val Leu
             35                  40                  45

Ile Asn Ser Arg Val Arg Pro Glu Arg Gln Arg Phe Thr Leu Ala His
 50                  55                  60

Glu Val Ser His Ala Leu Leu Leu Ala Asp Asp Asp Leu Leu Ser Asp
 65                  70                  75                  80

Leu His Asp Ala Phe Glu Gly Glu Arg Leu Glu Gln Val Ile Glu Thr
                 85                  90                  95

Leu Cys Asn Val Gly Ala Ala Ala Leu Leu Met Pro Asp Ala Leu Ile
                100                 105                 110

Asp Glu Val Leu Ala Arg His Gly Pro Ser Gly Gln Ala Leu Ala Asp
            115                 120                 125

Leu Ser Arg Arg Ala Glu Val Ser Ala Ser Ser Ala Leu Tyr Ala Leu
130                 135                 140

Ala Gly Arg Thr Thr Ala Pro Val Leu Tyr Ala Val Cys Ala Val Ser
145                 150                 155                 160

Arg Leu Glu Thr Glu Ala Glu Asp Thr Pro Ser Gly Lys Gly Leu Thr
                165                 170                 175
```

Val Arg Ala Ser Ser Gly Ala Pro Gly Val Arg Tyr Ser Leu Arg Pro
            180                 185                 190

Gly Thr Pro Ile Pro Asp Asp His Pro Val Ala Leu Ser Leu Ala Thr
            195                 200                 205

His Leu Pro Leu Ala Gln Glu Ser Tyr Val Pro Phe Arg Ser Gly Arg
            210                 215                 220

Arg Met Pro Ala Tyr Val Asp Ala Phe Pro Glu Arg Gln Arg Val Leu
225                 230                 235                 240

Val Ser Phe Ala Leu Gly Gln Arg Gly Arg Ala Gly Asp Gly Glu
                245                 250                 255

<210> SEQ ID NO 17
<211> LENGTH: 269
<212> TYPE: PRT
<213> ORGANISM: Deinococcus aquatilis

<400> SEQUENCE: 17

Met Arg Glu Leu Ala Thr Ala Tyr Val Gln His Leu Pro Gly Leu Asp
1               5                   10                  15

Thr His Ser Leu Met Ala Gly Leu Asp Gly Val Thr Leu Arg Phe Leu
            20                  25                  30

Pro Met Gly Glu Arg Asp Gly Ala Tyr Asp Pro Glu His His Val Ile
        35                  40                  45

Leu Ile Asn Ser Ala Val Arg Pro Ser Arg Gln Arg Phe Thr Leu Ala
    50                  55                  60

His Glu Ile Ser His Ala Leu Leu Leu Gly Asp Asp Asp Leu Leu Ser
65                  70                  75                  80

Asp Leu His Asp Ala Tyr Glu Gly Asp Arg Leu Glu Gly Val Ile Glu
                85                  90                  95

Thr Leu Cys Asn Val Gly Ala Ala Ala Ile Leu Met Pro Asp Thr Leu
            100                 105                 110

Ile Ala Glu Leu Leu Ser Arg Phe Gly Pro Thr Gly Arg Thr Leu Ala
        115                 120                 125

Glu Leu Ala Arg Arg Ala Asp Val Ser Ala Ser Ser Ala Leu Tyr Ala
130                 135                 140

Leu Ala Glu Arg Thr Glu Ala Pro Val Ile Tyr Ala Val Cys Ala Leu
145                 150                 155                 160

Ser Arg Val Asp Thr Glu Arg Glu Pro Asp Glu Asp Gly Ala Val
                165                 170                 175

Ala Pro Ser Thr Thr Lys Val Leu Thr Val Arg Ala Ser Ser Ala Ala
            180                 185                 190

Pro Gly Val Lys Tyr Ser Leu Arg Pro Gly Thr Pro Ile Pro Asp Thr
        195                 200                 205

His Pro Val Ala Val Ala Leu Asp Thr Asn Phe Pro Leu Ser Gln Glu
    210                 215                 220

Ser Tyr Val Pro Phe Arg Ser Gly Arg Lys Met Pro Ala Tyr Leu Asp
225                 230                 235                 240

Ala Phe Pro Glu Arg Gln Val Val Met Val Ser Phe Ala Leu Pro Val
                245                 250                 255

Pro Pro Ala Ser Ser Gln Ala Pro Lys Lys Asp Asp Asp
            260                 265

<210> SEQ ID NO 18
<211> LENGTH: 259
<212> TYPE: PRT

<213> ORGANISM: Deinococcus marmoris

<400> SEQUENCE: 18

Met Arg Glu Leu Ala Ala Asp Tyr Ala Arg Ala Leu Pro Gly Leu Asp
1               5                   10                  15

Thr His Ser Leu Met Ser Gly Leu Asp Gly Val Thr Leu Thr Phe Met
                20                  25                  30

Ala Met Gly Asp Arg Asp Gly Ala Tyr Asp Pro Glu His Arg Val Ile
            35                  40                  45

Leu Ile Asn Ser Arg Val Arg Pro Glu Arg Gln Arg Phe Thr Leu Ala
        50                  55                  60

His Glu Ile Gly His Ala Leu Leu Gly Asp Asp Leu Leu Ser
65                  70                  75                  80

Asp Leu His Asp Asn Phe Glu Gly Asp Arg Leu Glu Glu Val Ile Glu
                85                  90                  95

Thr Leu Cys Asn Val Ala Ala Ala Ile Leu Met Pro Glu Glu Leu
                100                 105                 110

Thr Ala Glu Leu Leu Thr Arg Phe Gly Pro Ser Gly Arg Ala Leu Ala
            115                 120                 125

Glu Leu Thr Arg Arg Ala Asp Val Ser Ala Ser Ala Leu Tyr Thr
130                 135                 140

Leu Ala Glu Arg Thr Asp Ala Pro Val Ile Tyr Ala Val Cys Ala Val
145                 150                 155                 160

Ala Arg Ile Asp Ala Glu Pro Gly Asp Ser Asp Glu Arg Pro Ser
                165                 170                 175

Gly Lys Ala Leu Thr Val Arg Ala Ser Ser Ala Ala Gly Val Lys
            180                 185                 190

Tyr Ser Leu Arg Pro Gly Thr Pro Ile Pro Asp Asp His Pro Val Ala
        195                 200                 205

Val Ala Leu Asp Thr Gly Ile Pro Ile Thr Gln Asp Ser Tyr Ile Pro
210                 215                 220

Phe Arg Ser Gly Arg Lys Met Pro Ala His Val Asp Val Phe Pro Glu
225                 230                 235                 240

Arg Asn Arg Val Leu Val Ser Phe Ala Leu Pro Val Lys Ala Ser Lys
                245                 250                 255

Asp Glu Ile

<210> SEQ ID NO 19
<211> LENGTH: 265
<212> TYPE: PRT
<213> ORGANISM: Deinococcus frigens

<400> SEQUENCE: 19

Met Arg Glu Leu Ala Ala Asp Tyr Ala Gln Ala Leu Pro Gly Leu Asp
1               5                   10                  15

Thr His Ser Leu Met Ser Gly Leu Asp Gly Val Thr Leu Thr Phe Met
                20                  25                  30

Ala Met Gly Asp Arg Asp Gly Ala Tyr Asp Pro Glu His Arg Val Ile
            35                  40                  45

Leu Ile Asn Ser Arg Val Arg Pro Glu Arg Gln Arg Phe Thr Leu Ala
        50                  55                  60

His Glu Ile Gly His Ala Leu Leu Gly Asp Asp Leu Leu Ser
65                  70                  75                  80

Asp Leu His Asp Asn Phe Glu Gly Asp Arg Leu Glu Glu Val Ile Glu
                85                  90                  95

```
Thr Leu Cys Asn Val Ala Ala Ala Ile Leu Met Pro Glu Asn Leu
            100                 105                 110

Ile Thr Glu Leu Leu Ala Arg Phe Gly Pro Ser Gly Arg Ala Leu Ala
        115                 120                 125

Glu Leu Ser Arg Arg Ala Asp Val Ser Ala Thr Ser Ala Leu Tyr Thr
    130                 135                 140

Leu Ala Glu Arg Thr Glu Ala Pro Val Ile Tyr Ala Val Cys Ala Val
145                 150                 155                 160

Ser Arg Leu Glu Ala Asp Pro Ala Asp Asp Ala Asp Ala Arg Pro
                165                 170                 175

Thr Gly Lys Ala Leu Thr Val Arg Ala Ser Ser Ala Ala Pro Gly Val
            180                 185                 190

Lys Tyr Ser Leu Arg Pro Gly Thr Pro Ile Pro Glu Asp His Pro Val
        195                 200                 205

Ala Val Ala Leu Asp Thr Arg Ile Pro Ile Thr Gln Asp Ser Tyr Ile
    210                 215                 220

Pro Phe Arg Ser Gly Arg Lys Met Pro Ala Tyr Val Asp Val Phe Pro
225                 230                 235                 240

Glu Arg His Arg Ala Leu Val Ser Phe Ala Leu Pro Val Lys Pro Ser
                245                 250                 255

Thr Val Gln Asp Arg Arg Glu Glu Val
            260                 265

<210> SEQ ID NO 20
<211> LENGTH: 266
<212> TYPE: PRT
<213> ORGANISM: Deinococcus swuensis

<400> SEQUENCE: 20

Met Arg Glu Leu Ala Ala Ala Tyr Ala Gln Ala Leu Pro Gly Leu Asp
1               5                   10                  15

Thr His Ser Leu Met Glu Gly Leu Asp Gly Val Thr Leu Thr Phe Met
            20                  25                  30

Ala Met Gly Asp Arg Asp Gly Ala Tyr Asp Pro Glu His Arg Val Ile
        35                  40                  45

Leu Ile Asn Ser Arg Val Arg Pro Glu Arg Gln Arg Phe Thr Leu Ala
    50                  55                  60

His Glu Ile Gly His Ala Leu Leu Leu Gly Asp Asp Leu Leu Ser
65                  70                  75                  80

Asp Leu His Asp Asn Phe Glu Gly Asp Arg Leu Glu Glu Val Ile Glu
                85                  90                  95

Thr Leu Cys Asn Val Ala Ala Ala Ile Leu Met Pro Glu Glu Leu
            100                 105                 110

Thr Ala Glu Leu Leu Ala Arg Phe Gly Pro Ser Gly Arg Ala Leu Ala
        115                 120                 125

Glu Leu Ser Arg Arg Ala Asp Val Ser Ala Thr Ser Ala Leu Tyr Thr
    130                 135                 140

Leu Ala Glu Arg Thr Glu Ala Pro Val Ile Tyr Ala Val Cys Ala Val
145                 150                 155                 160

Ala Arg Ile Asp Ala Gly Pro Gly Glu Arg Ser Asp Glu Pro Pro Ala
                165                 170                 175

Gly Lys Ala Leu Thr Val Arg Ala Ser Ser Pro Ala Pro Gly Val Lys
            180                 185                 190

Tyr Ser Leu Arg Pro Gly Thr Val Ile Pro Asp Asp His Pro Val Ala
```

195                 200                 205
Val Ala Leu Asp Thr Arg Ile Pro Ile Ala Gln Asp Ser Tyr Ile Pro
    210                 215                 220

Phe Arg Ser Gly Arg Lys Met Pro Ala Tyr Val Asp Val Phe Pro Glu
225                 230                 235                 240

Arg Asn Arg Ala Met Val Ser Phe Ala Leu Pro Val Arg Pro Gly Pro
                245                 250                 255

Ala Asp Ala Val Arg Glu Gln Glu Glu Val
            260                 265

<210> SEQ ID NO 21
<211> LENGTH: 281
<212> TYPE: PRT
<213> ORGANISM: Deinococcus deserti

<400> SEQUENCE: 21

Met Thr Asp Pro Ala Pro Pro Thr Ala Leu Ala Ala Ala Lys Ala
1               5                   10                  15

Arg Met Arg Glu Leu Ala Ala Ser Tyr Gly Ala Gly Leu Pro Gly Arg
                20                  25                  30

Asp Thr His Ser Leu Met His Gly Leu Asp Gly Ile Thr Leu Thr Phe
            35                  40                  45

Met Pro Met Gly Gln Arg Asp Gly Ala Tyr Asp Pro Glu His His Val
        50                  55                  60

Ile Leu Ile Asn Ser Gln Val Arg Pro Glu Arg Gln Arg Phe Thr Leu
65                  70                  75                  80

Ala His Glu Ile Ser His Ala Leu Leu Leu Gly Asp Asp Leu Leu
                85                  90                  95

Ser Asp Leu His Asp Glu Tyr Glu Gly Asp Arg Leu Glu Gln Val Ile
                100                 105                 110

Glu Thr Leu Cys Asn Val Gly Ala Ala Leu Leu Met Pro Ala Glu
            115                 120                 125

Leu Ile Asp Asp Leu Leu Thr Arg Phe Gly Pro Thr Gly Arg Ala Leu
130                 135                 140

Ala Glu Leu Ala Arg Arg Ala Asp Val Ser Ala Thr Ser Ala Leu Tyr
145                 150                 155                 160

Ala Leu Ala Glu Arg Thr Ala Pro Pro Val Ile Tyr Ala Val Cys Ala
                165                 170                 175

Leu Ser Arg Gln Glu Asp Glu Gly Glu Gly Gly Ala Lys Glu Leu
                180                 185                 190

Thr Val Arg Ala Ser Ser Ala Ser Ala Gly Val Lys Tyr Ser Leu Ser
                195                 200                 205

Ala Gly Thr Pro Val Pro Asp Asp His Pro Ala Ala Leu Ala Leu Asp
    210                 215                 220

Thr Arg Leu Pro Leu Ala Gln Asp Ser Tyr Val Pro Phe Arg Ser Gly
225                 230                 235                 240

Arg Arg Met Pro Ala Tyr Val Asp Ala Phe Pro Glu Arg Gln Arg Val
                245                 250                 255

Leu Val Ser Phe Ala Leu Pro Ala Gly Arg Ser Glu Pro Asp Ala Asp
            260                 265                 270

Lys Pro Glu Ala Pro Gly Asp Gln Ser
            275                 280

<210> SEQ ID NO 22
<211> LENGTH: 267

```
<212> TYPE: PRT
<213> ORGANISM: Deinococcus ficus

<400> SEQUENCE: 22

Met Arg Asp Leu Ala Ala Ala Tyr Ala Arg Thr Val Pro Gly Leu Asp
1               5                   10                  15

Ala His Ser Leu Met Glu Gly Leu Asp Gly Ile Ser Leu Thr Phe Met
            20                  25                  30

Pro Met Gly Asp Arg Asp Gly Ala Tyr Asp Pro Glu His Arg Val Ile
        35                  40                  45

Met Ile Asn Ser Ser Val Arg Pro Glu Arg Gln Arg Phe Thr Leu Ala
    50                  55                  60

His Glu Ile Ser His Ala Leu Leu Leu Gly Asp Asp Asp Leu Leu Ser
65                  70                  75                  80

Asp Ile His Asp Glu Tyr Glu Gly Asp Arg Leu Glu Gln Val Ile Glu
                85                  90                  95

Thr Leu Cys Asn Val Gly Ala Ala Ala Ile Leu Met Pro Asp Asp Leu
            100                 105                 110

Ile Ala Asp Val Leu Arg Arg Phe Gly Pro Thr Gly Arg Ala Leu Ala
        115                 120                 125

Glu Leu Ala Arg Arg Ala Asp Val Ser Ala Ser Ser Ala Leu Tyr Thr
    130                 135                 140

Leu Ala Glu Gln Thr Arg Asp Pro Val Ile Tyr Ala Val Cys Ala Val
145                 150                 155                 160

Thr Arg Leu Asp Gly Glu Asp Gly Glu Gly Pro Arg Lys Glu Leu Thr
                165                 170                 175

Val Arg Ala Ser Ser Gly Ala Pro Gly Val Lys Tyr Val Pro Gly Gln
            180                 185                 190

Asp Thr Val Ile Pro Ser Asp His Pro Ala Ala Val Thr Leu Asp Thr
        195                 200                 205

Gly Leu Pro Ala Asp Glu Asp Ser Tyr Val Pro Phe Arg Ser Gly Arg
    210                 215                 220

Arg Met Pro Ala Arg Val Asn Ala Phe Ala Glu Arg Gly Arg Val Leu
225                 230                 235                 240

Val Ser Phe His Leu Arg Asp Asp Lys Ala Gly Arg Pro Glu Ala Asp
                245                 250                 255

Gly Ala Leu Ser Asp Ser Ala Ala Ser Pro Ala
            260                 265

<210> SEQ ID NO 23
<211> LENGTH: 267
<212> TYPE: PRT
<213> ORGANISM: Deinococcus ficus

<400> SEQUENCE: 23

Met Arg Asp Leu Ala Ala Ala Tyr Ala Arg Thr Val Pro Gly Leu Asp
1               5                   10                  15

Ala His Ser Leu Met Glu Gly Leu Asp Gly Ile Ser Leu Thr Phe Met
            20                  25                  30

Pro Met Gly Asp Arg Asp Gly Ala Tyr Asp Pro Glu His Arg Val Ile
        35                  40                  45

Met Ile Asn Ser Ser Val Arg Pro Glu Arg Gln Arg Phe Thr Leu Ala
    50                  55                  60

His Glu Ile Ser His Ala Leu Leu Leu Gly Asp Asp Asp Leu Leu Ser
65                  70                  75                  80
```

```
Asp Ile His Asp Glu Tyr Glu Gly Asp Arg Leu Glu Gln Val Ile Glu
                85                  90                  95

Thr Leu Cys Asn Val Gly Ala Ala Ile Leu Met Pro Asp Asp Leu
            100                 105                 110

Ile Ala Asp Val Leu Arg Arg Phe Gly Pro Thr Gly Arg Ala Leu Ala
            115                 120                 125

Glu Leu Ala Arg Arg Ala Asp Val Ser Ala Ser Ser Ala Leu Tyr Thr
        130                 135                 140

Leu Ala Glu Gln Thr Arg Asp Pro Val Ile Tyr Ala Val Cys Ala Val
145                 150                 155                 160

Thr Arg Leu Asp Gly Glu Asp Gly Glu Gly Pro Arg Lys Glu Leu Thr
                165                 170                 175

Val Arg Ala Ser Ser Gly Ala Pro Gly Val Lys Tyr Val Pro Gly Gln
            180                 185                 190

Asp Thr Val Ile Pro Ser Asp His Pro Ala Ala Val Thr Leu Asp Thr
            195                 200                 205

Gly Leu Pro Ala Asp Glu Asp Ser Tyr Val Pro Phe Arg Ser Gly Arg
    210                 215                 220

Arg Met Pro Ala Arg Val Asn Ala Phe Ala Glu Arg Gly Arg Val Leu
225                 230                 235                 240

Val Ser Phe His Leu Arg Asp Asp Lys Ala Gly Arg Pro Glu Ala Asp
                245                 250                 255

Gly Ala Leu Ser Asp Ser Ala Ala Leu Pro Thr
            260                 265

<210> SEQ ID NO 24
<211> LENGTH: 263
<212> TYPE: PRT
<213> ORGANISM: Deinococcus wulumuqiensis

<400> SEQUENCE: 24

Met Arg Glu Leu Ala Ala Ala Tyr Gly Ala Gly Leu Pro Gly Arg Asp
1               5                   10                  15

Thr His Ser Leu Met Thr Gly Leu Pro Gly Val Glu Leu Arg Phe Leu
            20                  25                  30

Ser Leu Gly Trp Arg Asp Gly Ala Phe Asp Pro Glu His Asn Val Ile
        35                  40                  45

Val Ile Asn Ser Asp Val Arg Pro Glu Arg Gln Arg Phe Thr Leu Ala
    50                  55                  60

His Glu Ile Gly His Ala Leu Leu Leu Gly Asp Asp Asp Leu Leu Ser
65                  70                  75                  80

Asp Leu His Asp Ala Tyr Glu Gly Asp Glu Leu Glu Gln Lys Ile Glu
                85                  90                  95

Thr Leu Cys Asn Val Ala Ala Ala Ile Leu Met Pro Glu Pro Val
            100                 105                 110

Val Ala Glu Met Leu Glu Arg Phe Gly Ala Thr Gly Arg Ala Leu Ala
            115                 120                 125

Glu Leu Ala Lys Arg Ala Glu Val Ser Ala Ser Ser Ala Leu Tyr Ala
        130                 135                 140

Leu Ala Glu Ala Thr Pro Glu Pro Thr Ile Tyr Ala Val Cys Ala Leu
145                 150                 155                 160

Gly Lys Pro Pro Arg Glu Ala Leu Pro Ala Asp Pro Asp Ser Pro Ser
                165                 170                 175

Gly Glu Lys Val Leu Ser Val Arg Ala Ser Ser Ser Thr Arg Asp Val
            180                 185                 190
```

```
Lys Tyr Thr Leu Ala Ser Gly Thr Pro Ile Pro Gly Asp His Pro Ala
            195                 200                 205

Ala Val Ala Phe Glu Thr Gly Met Glu Val Lys Glu Ser Ser Tyr Val
            210                 215                 220

Pro Phe Arg Ser Gly Lys Lys Met Lys Ala Phe Val Ala Ala Tyr Pro
225                 230                 235                 240

Ser Arg Gly Leu Val Thr Val Ser Phe Gln Leu Asp Ala Ala Arg Leu
            245                 250                 255

Gly Lys Lys Glu Asp Arg Ala
            260

<210> SEQ ID NO 25
<211> LENGTH: 328
<212> TYPE: PRT
<213> ORGANISM: Deinococcus radiodurans

<400> SEQUENCE: 25

Met Pro Ser Ala Asn Val Ser Pro Pro Cys Pro Ser Gly Val Arg Gly
1               5                   10                  15

Gly Gly Met Gly Pro Lys Ala Lys Ala Glu Ala Ser Lys Pro His Pro
            20                  25                  30

Gln Ile Pro Val Lys Leu Pro Phe Val Thr Ala Pro Asp Ala Leu Ala
        35                  40                  45

Ala Ala Lys Ala Arg Met Arg Asp Leu Ala Ala Ala Tyr Val Ala Ala
    50                  55                  60

Leu Pro Gly Arg Asp Thr His Ser Leu Met Ala Gly Val Pro Gly Val
65                  70                  75                  80

Asp Leu Lys Phe Met Pro Leu Gly Trp Arg Asp Gly Ala Phe Asp Pro
                85                  90                  95

Glu His Asn Val Ile Leu Ile Asn Ser Ala Ala Arg Pro Glu Arg Gln
            100                 105                 110

Arg Phe Thr Leu Ala His Glu Ile Gly His Ala Ile Leu Leu Gly Asp
        115                 120                 125

Asp Asp Leu Leu Ser Asp Ile His Asp Ala Tyr Glu Gly Glu Arg Leu
    130                 135                 140

Glu Gln Val Ile Glu Thr Leu Cys Asn Val Ala Ala Ala Ile Leu
145                 150                 155                 160

Met Pro Glu Pro Val Ile Ala Glu Met Leu Glu Arg Phe Gly Pro Thr
                165                 170                 175

Gly Arg Ala Leu Ala Glu Leu Ala Lys Arg Ala Glu Val Ser Ala Ser
            180                 185                 190

Ser Ala Leu Tyr Ala Leu Thr Glu Gln Thr Pro Val Pro Val Ile Tyr
        195                 200                 205

Ala Val Cys Ala Pro Gly Lys Pro Arg Glu Gln Ala Ala Ser Asp
    210                 215                 220

Glu Asp Ala Gly Pro Ser Thr Glu Lys Val Leu Thr Val Arg Ala Ser
225                 230                 235                 240

Ser Ser Thr Arg Gly Val Lys Tyr Thr Leu Ala Ser Gly Thr Pro Val
                245                 250                 255

Pro Ala Asp His Pro Ala Ala Leu Ala Leu Ala Thr Gly Met Glu Val
            260                 265                 270

Arg Glu Glu Ser Tyr Val Pro Phe Arg Ser Gly Arg Lys Met Lys Ala
        275                 280                 285

Glu Val Asp Ala Tyr Pro Ser Arg Gly Ile Val Ala Val Ser Phe Glu
```

```
            290                 295                 300
Phe Asp Pro Ala Arg Leu Gly Arg Lys Asp Ser Glu Gln Ala Asp Arg
305                 310                 315                 320

Asp Glu Pro Gln Asp Ala Ala Gln
                325
```

<210> SEQ ID NO 26
<211> LENGTH: 275
<212> TYPE: PRT
<213> ORGANISM: Deinococcus radiodurans

<400> SEQUENCE: 26

```
Met Arg Asp Leu Ala Ala Ala Tyr Val Ala Ala Leu Pro Gly Arg Asp
1               5                  10                  15

Thr His Ser Leu Met Ala Gly Val Pro Gly Val Asp Leu Lys Phe Met
            20                  25                  30

Pro Leu Gly Trp Arg Asp Gly Ala Phe Asp Pro Glu His Asn Val Ile
        35                  40                  45

Leu Ile Asn Ser Ala Ala Arg Pro Glu Arg Gln Arg Phe Thr Leu Ala
    50                  55                  60

His Glu Ile Gly His Ala Ile Leu Leu Gly Asp Asp Leu Leu Ser
65                  70                  75                  80

Asp Ile His Asp Ala Tyr Glu Gly Glu Arg Leu Glu Gln Val Ile Glu
                85                  90                  95

Thr Leu Cys Asn Val Ala Ala Ala Ile Leu Met Pro Glu Pro Val
            100                 105                 110

Ile Ala Glu Met Leu Glu Arg Phe Gly Pro Thr Gly Arg Ala Leu Ala
        115                 120                 125

Glu Leu Ala Lys Arg Ala Glu Val Ser Ala Ser Ser Ala Leu Tyr Ala
    130                 135                 140

Leu Thr Glu Gln Thr Pro Val Pro Val Ile Tyr Ala Val Cys Ala Pro
145                 150                 155                 160

Gly Lys Pro Pro Arg Glu Gln Ala Ala Ser Asp Glu Asp Ala Gly Pro
                165                 170                 175

Ser Thr Glu Lys Val Leu Thr Val Arg Ala Ser Ser Thr Arg Gly
            180                 185                 190

Val Lys Tyr Thr Leu Ala Ser Gly Thr Pro Val Pro Ala Asp His Pro
        195                 200                 205

Ala Ala Leu Ala Leu Ala Thr Gly Met Glu Val Arg Glu Glu Ser Tyr
    210                 215                 220

Val Pro Phe Arg Ser Gly Arg Lys Met Lys Ala Glu Val Asp Ala Tyr
225                 230                 235                 240

Pro Ser Arg Gly Ile Val Ala Val Ser Phe Glu Phe Asp Pro Ala Arg
                245                 250                 255

Leu Gly Arg Lys Asp Ser Glu Gln Ala Asp Arg Asp Glu Pro Gln Asp
            260                 265                 270

Ala Ala Gln
        275
```

<210> SEQ ID NO 27
<211> LENGTH: 256
<212> TYPE: PRT
<213> ORGANISM: Deinococcus gobiensis

<400> SEQUENCE: 27

Met Arg Glu Leu Ala Ala Ala Tyr Ala Ala Arg Val Pro Ser Leu Asp

```
  1               5                  10                 15
Ala His Gly Leu Met Asp Gly Leu Asp Gly Val Gln Leu Arg Phe Met
                20                 25                 30

Pro Met Gly Gln Arg Asp Gly Ala Tyr Asp Pro Glu His His Val Ile
                35                 40                 45

Leu Ile Asn Ser Gln Val Arg Pro Glu Arg Gln Arg Phe Thr Leu Ala
        50                 55                 60

His Glu Ile Ser His Ala Leu Leu Leu Gly Asp Asp Leu Leu Ser
65                  70                 75                 80

Asp Leu His Asp Ser Phe Glu Gly Glu Arg Leu Glu Gln Val Ile Glu
                    85                 90                 95

Thr Leu Cys Asn Val Gly Ala Ala Leu Leu Met Pro Asp Ala Leu
                    100                105                110

Ile Ala Glu Leu Leu Glu Arg Phe Gly Ala Thr Gly Arg Ala Leu Ala
            115                120                125

Glu Leu Ser Arg Arg Ala Asp Val Ser Ala Ser Thr Ala Leu Tyr Ala
        130                135                140

Leu Ala Glu Arg Thr Pro Gly Ala Val Leu Tyr Ala Val Cys Thr Arg
145                 150                155                160

Ser Arg Leu Glu Thr Glu Thr Asp Asp Glu Asp Gly Ala Ala Ser
                    165                170                175

Gly Thr Ala Leu Thr Val Arg Val Ser Gly Ser Ala Gly Met Lys
                    180                185                190

Tyr Thr Leu Arg Pro Gly Thr Pro Ile Pro Ala Asp His Pro Val Gln
            195                200                205

Ala Ala Phe Glu Ser Asn Leu Pro Leu Thr Gly Pro Ser Tyr Val Pro
    210                215                220

Phe Arg Ser Gly Arg Lys Met Pro Ala Glu Val Asp Ala Phe Pro Val
225                 230                235                240

Arg Gly Arg Val Met Val Ser Phe Asp Leu Asn Gly Arg Gly Gly Thr
                    245                250                255
```

<210> SEQ ID NO 28
<211> LENGTH: 277
<212> TYPE: PRT
<213> ORGANISM: Deinococcus proteolyticus

<400> SEQUENCE: 28

```
Met Ser Val Pro Ala Pro Ala Phe Gln Glu Leu Lys Ala Arg Met Gln
1               5                  10                 15

Gly Leu Ala Ala Asp Tyr Ala Ala Ser Leu Pro Ala Gln Asp Met Ser
                20                 25                 30

Ser Met Ile Leu Gly Leu Glu Gly Ile Leu Pro Gln Val Pro Gln Val
                35                 40                 45

Lys Ala Val Pro Leu Gly Asp Arg Asp Gly Ala Tyr Asp Pro Glu His
        50                 55                 60

His Leu Ile Leu Ile Asp Ser Ala Ala Ser Pro Gln Arg Gln Arg Phe
65                  70                 75                 80

Thr Leu Ala His Glu Ile Ser His Ala Leu Leu Leu Asn Asp Asp
                    85                 90                 95

Leu Leu Ser Asp Val His Asp Leu Phe Glu Gly Glu Arg Leu Glu Gln
            100                105                110

Ala Ile Glu Thr Leu Cys Asn Val Gly Ala Ala Ala Met Leu Met Pro
        115                120                125
```

```
Pro Ala Leu Val His Asp Val Ile Gly Arg Phe Gly Pro Thr Gly Arg
    130                 135                 140

Ala Leu Ser Glu Leu Ala Arg Arg Ala Asp Val Ser Ala Ser Ala Ala
145                 150                 155                 160

Leu Tyr Thr Leu Ala Ala Glu Thr Glu Thr Ala Val Leu Tyr Ala Val
                165                 170                 175

Cys Gly Ala Gly Arg Ala Ala Gly Asp Ser Leu Gln Val Arg Ala Ser
                180                 185                 190

Ala Ala Ser Pro Ser Phe Pro Tyr Ser Leu Ser Pro Gly Thr Ala Ile
            195                 200                 205

Pro Ala Asp His Pro Val Gln Glu Ala Arg Ala Ser Gly Leu Pro Val
210                 215                 220

Glu Ala Val Ser Tyr Leu Pro Phe Arg Ser Gly Arg Arg Met Pro Ala
225                 230                 235                 240

Tyr Val Thr Ala Tyr Pro Ala Gly Gly Leu Val Ala Ala Ala Phe Ala
                245                 250                 255

Leu Gly Lys Ala Gln Leu Glu Arg Leu Gly Ala Ala Ser Ala Ala Gly
            260                 265                 270

Ala Ala Ala Glu Ser
            275

<210> SEQ ID NO 29
<211> LENGTH: 263
<212> TYPE: PRT
<213> ORGANISM: Deinococcus maricopensis

<400> SEQUENCE: 29

Met Thr His Asp Ala Asp Gly Leu Ala Pro His Lys Ala Arg Met Arg
1               5                   10                  15

Glu Leu Ala Arg Ala Tyr Ala Asp Ala Ala Pro Ser Arg Asp Ala His
                20                  25                  30

Gly Leu Thr Asp Pro Leu Gly Ala Lys Leu Val Tyr Met Asp Leu Gly
            35                  40                  45

Asp Arg Asp Gly Ala Tyr Asp Pro Glu His Gly Val Ile Leu Val Asn
    50                  55                  60

Ser Lys Val Gln Pro Gly Arg Gln Arg Phe Thr Leu Ala His Glu Ile
65                  70                  75                  80

Ser His Ala Leu Leu Leu Ala Asp Asp Leu Leu Ser Ala Leu His
                85                  90                  95

Asp Glu Tyr Asp Gly Asp Arg Leu Glu Gln Val Ile Glu Thr Leu Cys
                100                 105                 110

Asn Val Gly Ala Ala Ala Ile Leu Met Pro His Glu Leu Leu Thr Glu
            115                 120                 125

Leu Leu Thr Arg Phe Gly Ala Thr Gly Arg Ala Val Ala Glu Leu Ala
    130                 135                 140

Arg Arg Ala Asp Val Ser Val Ser Thr Ala Met Tyr Ala Leu Ala Glu
145                 150                 155                 160

Cys Val Thr Asp Arg Val Leu Phe Ala Val Ala Val Ala Ala Gly Gly
                165                 170                 175

Arg Leu Thr Val Arg Ala Ser Ala Ala Thr Asp Gly Val Lys Tyr Thr
                180                 185                 190

Leu Ser Asn Gly Thr Ala Ile Pro Asp Asp His Pro Ile His Asp Ala
            195                 200                 205

His Ala Thr His Leu Glu Ile Thr Ala Arg Ser Tyr Val Pro Phe Arg
    210                 215                 220
```

```
Ser Gly Arg Arg Leu Pro Ala Arg Val Asn Ala Tyr Pro Leu Arg Gly
225                 230                 235                 240

Arg Val Val Ala Ser Phe Thr Leu Asp Gln Pro Ala Pro Pro Asp Gly
            245                 250                 255

Thr Thr Pro Gly Ser Asp Ala
            260

<210> SEQ ID NO 30
<211> LENGTH: 236
<212> TYPE: PRT
<213> ORGANISM: Deinococcus pimensis

<400> SEQUENCE: 30

Met Arg Asp Leu Ala Arg Glu Phe Ala Ser Arg Gln Lys Val Arg Glu
1               5                   10                  15

Ala His Ala Leu Ala Glu Gly Leu Gly Ala Arg Leu Val Tyr Met Asp
            20                  25                  30

Leu Gly Glu Arg Asp Gly Ala Tyr Asp Pro Glu His Ala Val Ile Leu
        35                  40                  45

Val Asn Gln Thr His Ser Pro Gln Arg Gln Arg Phe Thr Leu Ala His
50                  55                  60

Glu Val Ser His Ala Leu Leu Leu Gly Asp Glu Asp Leu Leu Ser Asp
65                  70                  75                  80

Leu His Asp Leu Phe Glu Gly Asp Ala Leu Glu Asn Ala Ile Glu Thr
                85                  90                  95

Leu Cys Asn Val Gly Ala Ala Thr Ile Leu Ile Ser Asp Glu Glu Leu
            100                 105                 110

Arg Ala Ala Val Glu Arg His Gly Ala Ser Gly Ala Ala Ile Ala Asp
        115                 120                 125

Val Ala Arg Arg Ala Asp Val Ser Ala Ala Val Ala Met Tyr Ala Leu
130                 135                 140

Ala Asp Phe Val Lys Thr Pro Ala Val Phe Ala Val Cys Thr Gly Gly
145                 150                 155                 160

His Asn Arg Pro Leu Leu Val Gln Ser Ser Ala Ser Thr Ser Ser Met
                165                 170                 175

Arg Tyr Ser Leu Arg Pro Gly Thr Val Ile Pro Asp Gly His Pro Val
            180                 185                 190

Asp Thr Ala Phe Arg Thr Gly Leu Pro Ile Glu Glu Pro Ser Phe Phe
        195                 200                 205

Pro Phe Arg Ser Gly Lys Lys Met Pro Ala Tyr Val Thr Ala Tyr Pro
    210                 215                 220

Ile Lys Thr Arg Val Leu Cys Ser Phe Glu Glu Arg
225                 230                 235

<210> SEQ ID NO 31
<211> LENGTH: 264
<212> TYPE: PRT
<213> ORGANISM: Deinococcus peraridilitoris

<400> SEQUENCE: 31

Met Thr Ala Asn Glu Thr Gln Thr His Ser Phe Glu Ala His Lys Ala
1               5                   10                  15

Arg Met Arg Ala Leu Ala Arg Glu Phe Gly Arg Ala His Ala Ser Lys
            20                  25                  30

Asp Pro His Ala Leu Ala Glu Gly Leu Gly Ala Arg Leu Ala Tyr Met
        35                  40                  45
```

```
Asp Leu Gly Glu Arg Asp Gly Ala Tyr Asp Pro Glu His Gly Val Ile
        50                  55                  60

Leu Val Asn Gly Ser His Ser Arg Glu Arg Gln Arg Phe Thr Leu Ala
 65                  70                  75                  80

His Glu Val Ser His Ala Leu Leu Leu Ala Asp Glu Asp Leu Leu Ser
                 85                  90                  95

Asp Leu His Asp Thr Phe Asp Gly Glu Ala Leu Glu Asn Ala Ile Glu
            100                 105                 110

Thr Leu Cys Asn Val Gly Ala Ala Thr Ile Leu Ile Ser Asp Asp Asp
            115                 120                 125

Leu Arg Ser Ala Leu Glu Arg Phe Gly Thr Ser Gly Gln Thr Ile Ala
130                 135                 140

Glu Val Ala Arg Arg Ala Asp Val Ser Ala Pro Val Ala Leu Tyr Ala
145                 150                 155                 160

Leu Ala Asp Phe Val Arg Thr Pro Ala Met Phe Val Val Cys Ala Pro
                165                 170                 175

Asp Ser Ala Leu Arg Gly His Ala Arg Phe Ser Pro Gly Arg Gly Val
            180                 185                 190

Val Val Gln His Ser Ala Ser Thr Ala Ser Met Arg Tyr Ser Leu Ser
        195                 200                 205

Pro Gly Thr Pro Ile Pro Glu Gly His Thr Val Asp Thr Ala Phe Arg
210                 215                 220

Thr Gly Leu Pro Ile Asp Glu Val Ser Phe Phe Pro Phe Arg Ser Gly
225                 230                 235                 240

Lys Arg Met Pro Ala Ile Val Ser Ala Phe Pro Gln Arg Gly Arg Val
                245                 250                 255

Leu Cys Ala Phe Glu Glu Arg Gly
            260

<210> SEQ ID NO 32
<211> LENGTH: 247
<212> TYPE: PRT
<213> ORGANISM: Deinococcus peraridilitoris

<400> SEQUENCE: 32

Met Arg Ala Leu Ala Arg Glu Phe Gly Arg Ala His Ala Ser Lys Asp
 1               5                  10                  15

Pro His Ala Leu Ala Glu Gly Leu Gly Ala Arg Leu Ala Tyr Met Asp
                20                  25                  30

Leu Gly Glu Arg Asp Gly Ala Tyr Asp Pro Glu His Gly Val Ile Leu
            35                  40                  45

Val Asn Gly Ser His Ser Arg Glu Arg Gln Arg Phe Thr Leu Ala His
 50                  55                  60

Glu Val Ser His Ala Leu Leu Leu Ala Asp Glu Asp Leu Leu Ser Asp
 65                  70                  75                  80

Leu His Asp Thr Phe Asp Gly Glu Ala Leu Glu Asn Ala Ile Glu Thr
                85                  90                  95

Leu Cys Asn Val Gly Ala Ala Thr Ile Leu Ile Ser Asp Asp Asp Leu
            100                 105                 110

Arg Ser Ala Leu Glu Arg Phe Gly Thr Ser Gly Gln Thr Ile Ala Glu
        115                 120                 125

Val Ala Arg Arg Ala Asp Val Ser Ala Pro Val Ala Leu Tyr Ala Leu
130                 135                 140

Ala Asp Phe Val Arg Thr Pro Ala Met Phe Val Val Cys Ala Pro Asp
```

```
                145                 150                 155                 160
        Ser Ala Leu Arg Gly His Ala Arg Phe Ser Pro Gly Arg Gly Val Val
                        165                 170                 175

Val Gln His Ser Ala Ser Thr Ala Ser Met Arg Tyr Ser Leu Ser Pro
                        180                 185                 190

Gly Thr Pro Ile Pro Glu Gly His Thr Val Asp Thr Ala Phe Arg Thr
                        195                 200                 205

Gly Leu Pro Ile Asp Glu Val Ser Phe Phe Pro Phe Arg Ser Gly Lys
                        210                 215                 220

Arg Met Pro Ala Ile Val Ser Ala Phe Pro Gln Arg Gly Arg Val Leu
        225                 230                 235                 240

Cys Ala Phe Glu Glu Arg Gly
                        245

<210> SEQ ID NO 33
<211> LENGTH: 247
<212> TYPE: PRT
<213> ORGANISM: Deinococcus misasensis

<400> SEQUENCE: 33

Met Asp Pro Lys Pro Gln His Lys Ala Arg Met Arg Glu Leu Ala Leu
        1               5                   10                  15

Asp Phe Ala Arg Thr His Gln Ala Arg Asp Leu Tyr Ser Leu Gly Glu
                        20                  25                  30

Ala Ala Gly Thr Lys Leu Val Phe Met Asp Leu Gly Glu Arg Asp Gly
                        35                  40                  45

Ala Tyr Asp Pro Glu His Lys Ala Ile Ile Ile Asn Asn Thr Arg Asp
                        50                  55                  60

Leu Asn Arg Gln Lys Phe Thr Leu Ala His Glu Ile Ala His Ala Leu
        65                  70                  75                  80

Leu Leu Asp Asp Asp Leu Leu Ser Asp Ile His Glu Asp Phe Glu
                        85                  90                  95

Gly Asp Ser Leu Glu Gln Val Ile Glu Lys Leu Cys Asp Trp Gly Ala
                        100                 105                 110

Ala Asn Ile Leu Ile Glu Pro Glu Thr Leu Gln Glu Val Leu Asn Arg
                        115                 120                 125

His Gly Ile Ser Ala Gln Gly Val Met Asp Leu Ser Arg Lys Ala His
                        130                 135                 140

Ile Ser Leu Arg Ser Ala Met Val Ala Ile Ala Glu Gln Ala Gln Asn
        145                 150                 155                 160

Pro Thr Leu Ile Val Leu Phe Gln Pro Ala Ala Pro Gln Lys Pro Leu
                        165                 170                 175

Val Val Asn Phe Thr Ala Gln Asn Ala Ala Phe Lys Tyr Thr Leu Thr
                        180                 185                 190

Pro Gly Gln Val Leu Val Gln Asp His Pro Val Gln Val Ser Phe Glu
                        195                 200                 205

Thr Arg Leu Pro Leu Glu Glu Asp Ser Tyr Val Pro Phe Ala Ser Gly
                        210                 215                 220

Lys Lys Met Pro Ala His Leu Thr Thr Tyr Pro Glu Lys Met Arg Val
        225                 230                 235                 240

Leu Ala Val Phe Lys Thr Pro
                        245

<210> SEQ ID NO 34
<211> LENGTH: 29
```

```
<212> TYPE: DNA
<213> ORGANISM: Artificial Sequence
<220> FEATURE:
<223> OTHER INFORMATION: 0395-F

<400> SEQUENCE: 34
accactagta tgacgcaggg ccagacccc                                    29

<210> SEQ ID NO 35
<211> LENGTH: 29
<212> TYPE: DNA
<213> ORGANISM: Artificial Sequence
<220> FEATURE:
<223> OTHER INFORMATION: 0395-R

<400> SEQUENCE: 35
acccatatgt cagacacccg actcatcct                                    29

<210> SEQ ID NO 36
<211> LENGTH: 40
<212> TYPE: DNA
<213> ORGANISM: Artificial Sequence
<220> FEATURE:
<223> OTHER INFORMATION: b1-L154V-F

<400> SEQUENCE: 36
gggcgtgcgg tggctgagct ggcgcggcgg gcagacgtga                        40

<210> SEQ ID NO 37
<211> LENGTH: 40
<212> TYPE: DNA
<213> ORGANISM: Artificial Sequence
<220> FEATURE:
<223> OTHER INFORMATION: c1-L154V-R

<400> SEQUENCE: 37
tcacgtctgc ccgccgcgcc agctcagcca ccgcacgccc                        40

<210> SEQ ID NO 38
<211> LENGTH: 40
<212> TYPE: DNA
<213> ORGANISM: Artificial Sequence
<220> FEATURE:
<223> OTHER INFORMATION: b2-A155S-F

<400> SEQUENCE: 38
gggcgtgcgc tgagcgagct ggcgcggcgg gcagacgtga                        40

<210> SEQ ID NO 39
<211> LENGTH: 40
<212> TYPE: DNA
<213> ORGANISM: Artificial Sequence
<220> FEATURE:
<223> OTHER INFORMATION: c2-A155S-R

<400> SEQUENCE: 39
tcacgtctgc ccgccgcgcc agctcgctca ccgcacgccc                        40

<210> SEQ ID NO 40
<211> LENGTH: 40
<212> TYPE: DNA
<213> ORGANISM: Artificial Sequence
<220> FEATURE:
<223> OTHER INFORMATION: b3-L157V-F

<400> SEQUENCE: 40
```
gggcgtgcgc tggctgaggt ggcgcggcgg gcagacgtga         40

<210> SEQ ID NO 41
<211> LENGTH: 40
<212> TYPE: DNA
<213> ORGANISM: Artificial Sequence
<220> FEATURE:
<223> OTHER INFORMATION: c3-L157V-R

<400> SEQUENCE: 41
tcacgtctgc ccgccgcgcc agcacagcca ccgcacgccc         40

<210> SEQ ID NO 42
<211> LENGTH: 40
<212> TYPE: DNA
<213> ORGANISM: Artificial Sequence
<220> FEATURE:
<223> OTHER INFORMATION: b4-A158S-F

<400> SEQUENCE: 42
gggcgtgcgc tggctgagct gagccggcgg gcagacgtga         40

<210> SEQ ID NO 43
<211> LENGTH: 40
<212> TYPE: DNA
<213> ORGANISM: Artificial Sequence
<220> FEATURE:
<223> OTHER INFORMATION: c4-A158S-R

<400> SEQUENCE: 43
tcacgtctgc ccgcccgctc agctcagcca ccgcacgccc         40

<210> SEQ ID NO 44
<211> LENGTH: 40
<212> TYPE: DNA
<213> ORGANISM: Artificial Sequence
<220> FEATURE:
<223> OTHER INFORMATION: b5-R159K-F

<400> SEQUENCE: 44
gggcgtgcgc tggctgagct ggcgaagcgg gcagacgtga         40

<210> SEQ ID NO 45
<211> LENGTH: 40
<212> TYPE: DNA
<213> ORGANISM: Artificial Sequence
<220> FEATURE:
<223> OTHER INFORMATION: c5-R159K-R

<400> SEQUENCE: 45
tcacgtctgc ccgcttcgcc agctcagcca gcgcacgccc         40

<210> SEQ ID NO 46
<211> LENGTH: 28
<212> TYPE: DNA
<213> ORGANISM: Artificial Sequence
<220> FEATURE:
<223> OTHER INFORMATION: a-dr0167-F

<400> SEQUENCE: 46
taactagtgt gcccagtgcc aacgtcag                       28

<210> SEQ ID NO 47
<211> LENGTH: 25
<212> TYPE: DNA
<213> ORGANISM: Artificial Sequence

```
<220> FEATURE:
<223> OTHER INFORMATION: d-dr0167-R

<400> SEQUENCE: 47
tacatatgtc actgtgcagc gtcct                                          25

<210> SEQ ID NO 48
<211> LENGTH: 42
<212> TYPE: DNA
<213> ORGANISM: Artificial Sequence
<220> FEATURE:
<223> OTHER INFORMATION: b1-A181S-F

<400> SEQUENCE: 48
ggccccaccg ggcgcgccct cagcgaactc gccaagcggg cc                       42

<210> SEQ ID NO 49
<211> LENGTH: 42
<212> TYPE: DNA
<213> ORGANISM: Artificial Sequence
<220> FEATURE:
<223> OTHER INFORMATION: c1-A181S-R

<400> SEQUENCE: 49
ggcccgcttg gcgagttcgc tgagggcgcg cccggtgggg cc                       42

<210> SEQ ID NO 50
<211> LENGTH: 42
<212> TYPE: DNA
<213> ORGANISM: Artificial Sequence
<220> FEATURE:
<223> OTHER INFORMATION: b2-A184S-F

<400> SEQUENCE: 50
ggccccaccg ggcgcgccct cgccgaactc agcaagcggg cc                       42

<210> SEQ ID NO 51
<211> LENGTH: 42
<212> TYPE: DNA
<213> ORGANISM: Artificial Sequence
<220> FEATURE:
<223> OTHER INFORMATION: c2-A184S-R

<400> SEQUENCE: 51
ggcccgcttg ctgagttcgg cgagggcgcg cccggtgggg cc                       42

<210> SEQ ID NO 52
<211> LENGTH: 27
<212> TYPE: DNA
<213> ORGANISM: Artificial Sequence
<220> FEATURE:
<223> OTHER INFORMATION: a-CA2805-F

<400> SEQUENCE: 52
taactagtat gcgcgagctg gcggcgg                                        27

<210> SEQ ID NO 53
<211> LENGTH: 26
<212> TYPE: DNA
<213> ORGANISM: Artificial Sequence
<220> FEATURE:
<223> OTHER INFORMATION: d-CA2805-R

<400> SEQUENCE: 53
tacatatggt gagagggaga cgcgct                                         26
```

```
<210> SEQ ID NO 54
<211> LENGTH: 39
<212> TYPE: DNA
<213> ORGANISM: Artificial Sequence
<220> FEATURE:
<223> OTHER INFORMATION: b1-S131A-F

<400> SEQUENCE: 54
cgcgccctgg ccgagttggc ccgccgcgcc gacgtgagt                    39

<210> SEQ ID NO 55
<211> LENGTH: 39
<212> TYPE: DNA
<213> ORGANISM: Artificial Sequence
<220> FEATURE:
<223> OTHER INFORMATION: c1-S131A-R

<400> SEQUENCE: 55
actcacgtcg gcgcggcggg ccaactcggc cagggcgcg                    39

<210> SEQ ID NO 56
<211> LENGTH: 6
<212> TYPE: PRT
<213> ORGANISM: Artificial Sequence
<220> FEATURE:
<223> OTHER INFORMATION: artificial modification on functional domain
      motif in SEQ ID NO.3

<400> SEQUENCE: 56

Val Ala Glu Leu Ala Arg
 1               5

<210> SEQ ID NO 57
<211> LENGTH: 6
<212> TYPE: PRT
<213> ORGANISM: Artificial Sequence
<220> FEATURE:
<223> OTHER INFORMATION: artificial modification on functional domain
      motif in SEQ ID NO.3

<400> SEQUENCE: 57

Leu Ala Glu Val Ala Arg
 1               5

<210> SEQ ID NO 58
<211> LENGTH: 6
<212> TYPE: PRT
<213> ORGANISM: Artificial Sequence
<220> FEATURE:
<223> OTHER INFORMATION: artificial modification on functional domain
      motif in SEQ ID NO.3

<400> SEQUENCE: 58

Leu Ala Glu Val Ala Lys
 1               5
```

IRRE PROTEIN FUNCTIONAL DOMAIN FOR IMPROVING ANTI-OXIDATION CAPABILITY OF CELL AND APPLICATION THEREOF

CROSS REFERENCE TO RELATED APPLICATIONS

This application is the national phase entry of International Application No. PCT/CN2016/081403, filed on May 9, 2016, which is based upon and claims priority to Chinese Patent Application No. CN 2015102367908, filed on May 11, 2015, the entire contents of which are incorporated herein by reference.

FIELD OF THE INVENTION

This invention relates to a gene functional domain for enhancing cell oxidation resistance, specially relates to *Deinococcus geothermalis* Dgeo0395 with optimized domain and its homologous proteins thereof, as well as the use of this protein to enhance the resistance of host against desiccation, oxidation and ultraviolet irradiation.

BACKGROUND OF THE INVENTION

IrrE is a specific global regulatory factor of *Deinococcus*, which plays a central regulatory role in DNA damage repair, stress responsive and protective pathways. IrrE can activate catalase of *Deinococcus*, and then enhance to clean up the intracellular oxygen free radical, activate pathways of multiple proteins synthesis and protein cyclic utilization; in addition, it can activate modification system of transcription, translation and post-translation, and then generate more defensive proteins as well as accelerate degradation of the damaged proteins, in order that cell can recover faster from damage of ionizing radiation. It's shown by research results that, IrrE protein of *D. radiodurans* can significantly strengthen salt tolerance of model organisms like *Escherichia coli* and tobacco.

The important regulatory protein IrrE of *Deinococcus geothermalis* is coded by Dgeo0395 gene. According to information in NCBI (the US National Center for Biotechnology Information) database, it's discovered currently that there are 23 homologous proteins of IrrE in total. The protein ID and corresponding amino acid sequences of the 23 homologous proteins of IrrE in NCBI (https://www.ncbi.nlm.nih.gov/protein/) are as following.

| Protein ID | Amino acid sequences recorded in the NCBI |
|---|---|
| WP_019588002.1 (SEQ ID NO.11) | 1 mrelasayvr glpgldthsl msgldatltf mpmgdrdgay dpehrvvlin srvrperqrf 61 tlaheishal llgdddllsd lhdayegerl eqvleticnv gaaailmpda lidellarfg 121 psgralaela rradvsassa lyalaertaa pvlyavcava rleaepgdee rptgkaltvr 181 asggapsvky slrpgtlipa ehpvavalet hlpiaqesyv pfrsgrrmpa yvdafperqr 241 vmvsftltpr ptkggesdep ag |
| EYB67551.1 (SEQ ID NO.12) | 1 mtqgrtptep isadaspdag alapakarmr elaaayvqgl pgldthslms gldatltflp 61 mgdrdgaydp ehrvvlinsr vrperqrftl aheishalll gdddllsdlh dayegerleq 121 vietlcniga aailmpeali devvsrfgps gralaelarr advsassaly alaerttapv 181 lyavcavtrl aepgeerpsd kaltvrasgg apgykyslrp gtripddhpv avalethlpm |
| WP_034358392.1 (SEQ ID NO.13) | 241 tqesyvpfrs grrmpayvda fperqrvlvs falmpraarg seddepvt 1 mrelaaayvq glpgldthsl msgldatltf lpmgdrdgay dpehrvvlin srvrperqrf 61 tlaheishal llgdddllsd lhdayegerl eqvietlcni gaaailmpea lidevvsrfg 121 psgralaela rradvsassa lyalaertta pvlyavcavt rlaepgeerp sdkaltvras 181 ggapgykysl rpgtripddh pvavalethl pmtqesyvpf rsgrrmpayv dafperqrvl 241 vsfalmpraa rgseddepvt |
| WP_034387888.1 (SEQ ID NO.14) | 1 mrelaaayar rlpgldthsl msgldatlkf mpmgdrdgay dpehrvvlin sqvrperqrf 61 tlaheishal llgdddllsd lhdafegerl eqvietlcnv gaaallmpea lvdevmarfg 121 ptgralaels rradvsassa lyalaertta pvlyavcalt rpevegsdea rpaekvltvr 181 vsggapgvky slrpgtvipd dhpvaaalet hlpigqesyv pfrsgrrmpa yvdafperqr 241 vlvsfalrpr pakggedhdp ea |
| WP_034408305.1 (SEQ ID NO.15) | 1 mrelaatyas glpgrdthsl lagldatlrf lpmgerdgay dpehrvvlin srvrperqrf 61 tlahevshal lladddllsd lhdafegerl eqvietlcnv gaaallmpda lidevlarhg 121 psgqaladls rraevsassa lyalvgrtsa pvlyavcavs rleteaeetp pgkgltvras 181 sgapgvrysl rpgtpipddh pvalslathl plaqesyvpf rsgrrmpayv dafperqrvl 241 vsfalgqrgr vgedge |
| WP_034406652.1 (SEQ ID NO.16) | 1 mrelaatyas glpgrdthsl lagldatlrf lpmgerdgay dpehrvvlin srvrperqrf 61 tlahevshal lladddllsd lhdafegerl eqvietlcnv gaaallmpda lidevlarhg 121 psgqaladls rraevsassa lyalagrtta pvlyavcavs rleteaedtp sgkgltvras 181 sgapgvrysl rpgtpipddh pvalslathl plaqesyvpf rsgrrmpayv dafperqrvl 241 vsfalgqrgr agedge |
| WP_040381646.1 (SEQ ID NO.17) | 1 mrelatayvq hlpgldthsl magldgvtlr flpmgerdga ydpehhvili nsavrpsrqr 61 ftlaheisha lllgdddlls dlhdayegdr legvietlcn vgaaailmpd tliaellsrf 121 gptgrtlael arradvsass alyalaerte apviyavcal srvdteerep dedgavapst 181 tkvltvrass aapgvkyslr pgtpipdthp vavaldtnfp lsqesyvpfr sgrkmpayld 241 afperqvvmv sfalpvppas sqapkkddd |
| WP_029483991.1 (SEQ ID NO.18) | 1 mrelaadyar alpgldthsl msgldgvtlt fmamgdrdga ydpehrvili nsrvrperqr 61 ftlaheigha lllgdddlls dlhdnfegdr leevietlcn vaaaailmpe eltaelltrf 121 gpsgralael trradvsass alytlaertd apviyavcav aridaepgds deerpsgkal 181 tvrasssaag vkyslrpgtp ipddhpvava ldtgipitqd syipfrsgrk mpahvdvfpe 241 mrvlvsfal pvkaskdei |
| WP_034419261.1 (SEQ ID NO.19) | 1 mrelaadyaq alpgldthsl msgldgvtlt fmamgdrdga ydpehrvili nsrvrperqr 61 ftlaheigha lllgdddlls dlhdnfegdr leevietlcn vaaaailmpe nlitellarf 121 gpsgralael srradvsats alytlaerte apviyavcav srleadpadd addarptgka 181 ltvrassaap gvkyslrpgt pipedhpvav aldtripitq dsyipfrsgr kmpayvdvfp 241 erhralvsfa lpvkpstvqd rreev |
| WP_039685814.1 (SEQ ID NO.20) | 1 mrelaaayaq alpgldthsl megldgvtlt fmamgdrdga ydpehrvili nsrvrperqr 61 ftlaheigha lllgdddlls dlhdnfegdr leevietlcn vaaaailmpe eltaellarf 121 gpsgralael srradvsats alytlaerte apviyavcav aridagpger sdeppagkal 181 tvrasspapg vkyslrpgtv ipddhpvava ldtripiaqd syipfrsgrk mpayvdvfpe 241 mramvsfal pvrpgpadav reqeev |

| Protein ID | Amino acid sequences recorded in the NCBI |
|---|---|
| WP_012692245.1 (SEQ ID NO.21) | 1 mtdpapppta laaakarmre laasygaglp grdthslmhg ldgitltfmp mgqrdgaydp<br>61 ehhvilinsq vrperqrftl aheishalll gdddllsdlh deyegdrleq vietlcnvga<br>121 aallmpaeli ddlltrfgpt gralaelarr advsatsaly alaertappv iyavcalsrq<br>181 edegegggak eltvrassas agvkyslsag tpvpddhpaa laldtrlpla qdsyvpfrsg<br>241 rrmpayvdaf perqrylvsf alpagrsepd adkpeapgdq s |
| WP_043817964.1 (SEQ ID NO.22) | 1 mrdlaaayar tvpgldahsl megldgislt fmpmgdrdga ydpehrvimi nssvrperqr<br>61 ftlaheisha lllgdddlls dihdeyegdr leqvietlcn vgaaailmpd dliadvlrrf<br>121 gptgralael arradvsass alytlaeqtr dpviyavcav trldgedgeg prkeltvras<br>181 sgapgykyvp gqdtvipsdh paavtldtgl padedsyvpf rsgrrmparv nafaergrvl<br>241 vsfhlrddka grpeadgals dsaaspa |
| WP_043779788.1 (SEQ ID NO.23) | 1 mrdlaaayar tvpgldahsl megldgislt fmpmgdrdga ydpehrvimi nssvrperqr<br>61 ftlaheisha lllgdddlls dihdeyegdr leqvietlcn vgaaailmpd dliadvlrrf<br>121 gptgralael arradvsass alytlaeqtr dpviyavcav trldgedgeg prkeltvras<br>181 sgapgykyvp gqdtvipsdh paavtldtgl padedsyvpf rsgrrmparv nafaergrvl<br>241 vsfhlrddka grpeadgals dsaalpt |
| WP_017871397.1 (SEQ ID NO.24) | 1 mrelaaayga glpgrdthsl mtglpgvelr flslgwrdga fdpehnvivi nsdvrperqr<br>61 ftlaheigha lllgdddlls dlhdayegde leqkietlcn vaaaailmpe pvvaemlerf<br>121 gatgralael akraevsass alyalaeatp eptiyavcal gkpprealpa dpdspsgekv<br>181 lsvrassstr dvkytlasgt pipgdhpaav afetgmevke ssyvpfrsgk kmkafvaayp<br>241 srglytysfq ldaarlgkke dra |
| WP_010886813.1 (SEQ ID NO.25) | 1 mpsanvsppc psgvrgggmg pkakaeaskp hpqipvklpf vtapdalaaa karmrdlaaa<br>61 yvaalpgrdt hslmagvpgy dlkfmplgwr dgafdpehnv ilinsaarpe rqrftlahei<br>121 ghaillgddd llsdihdaye gerleqviet lcnvaaaail mpepviaeml erfgptgral<br>181 aelakraevs assalyalte qtpvpviyav capgkppreq aasdedagps tekvltvras<br>241 sstrgykvtl asgtpvpadh paalalatgm evreesyvpf rsgrkmkaev daypsrgiva<br>301 vsfefdparl grkdseqadr depqdaaq |
| WP_034350714.1 (SEQ ID NO.26) | 1 mrdlaaayva alpgrdthsl magvpgvdlk fmplgwrdga fdpehnvili nsaarperqr<br>61 ftlaheigha illgdddlls dihdayeger leqvietlcn vaaaailmpe pviaemlerf<br>121 gptgralael akraevsass alyalteqtp vpviyavcap gkppreqaas dedagpstek<br>181 vltvrassst rgvkytlasg tpvpadhpaa lalatgmevr eesyvpfrsg rkmkaevday<br>241 psrgivavsf efdparlgrk dseqadrdep qdaaq |
| WP_014686212.1 (SEQ ID NO.27) | 1 mrelaaayaa rvpsldahgl mdgldgvqlr fmpmgqrdga ydpehhvili nsqvrperqr<br>61 ftlaheisha lllgdddlls dlhdsfeger leqvietlcn vgaaallmpd aliaellerf<br>121 gatgralael srradvsast alyalaertp gavlyavctr srletetdde dggaasgtal<br>181 tvrvsggsag mkytlrpgtp ipadhpvqaa fesnlpltgp syvpfrsgrk mpaevdafpv<br>241 rgrvmvsfdl ngrggt |
| WP_013615637.1 (SEQ ID NO.28) | 1 msvpapafqe lkarmqglaa dyaaslpaqd mssmilgleg ilpqvpqvka vplgdrdgay<br>61 dpehhlilid saaspqrqrf tlaheishal llndddllsd vhdlfegerl eqaietlcnv<br>121 gaaamlmppa lvhdvigrfg ptgralsela rradvsasaa lytlaaetet avlyavcgag<br>181 raagdslqvr asaaspsfpy slspgtaipa dhpvqearas glpveavsyl pfrsgrrmpa<br>241 yvtaypaggl vaaafalgka qlerlgaasa agaaaes |

| Protein ID | Amino acid sequences recorded in the NCBI |
|---|---|
| WP_013556095.1 (SEQ ID NO.29) | 1 mthdadglap hkarmrelar ayadaapsrd ahgltdplga klvymdlgdr dgaydpehgv<br>61 ilynskyqpg rqrftlahei shallladdd llsalhdeyd gdrleqviet lcnvgaaail<br>121 mphelltell trfgatgrav aelarradvs vstamyalae cvtdrvlfav avaaggrltv<br>181 rasaatdgvk ytlsngtaip ddhpihdaha thleitarsy vpfrsgrrlp arvnayplrg<br>241 rvvasftldq pappdgttpg sda |
| WP_027482769.1 (SEQ ID NO.30) | 1 mrdlarefas rqkvreahal aeglgarlvy mdlgerdgay dpehavilvn qthspqrqrf<br>61 tlahevshal llgdedllsd lhdlfegdal enaietlcnv gaatilisde elraaverhg<br>121 asgaaiadva rradvsaava myaladfvkt pavfavctgg hnrpllvqss astssmrysl<br>181 rpgtvipdgh pvdtafrtgl pieepsffpf rsgkkmpayv taypiktrvl csfeer |
| AFZ68369.1 (SEQ ID NO.31) | 1 mtanetqths feahkarmra larefgraha skdphalaeg lgarlaymdl gerdgaydpe<br>61 hgvilvngsh srerqrftla hevshallla dedllsdlhd tfdgealena ietlcnvgaa<br>121 tilisdddlr salerfgtsg qtiaevarra dvsapvalya ladfvrtpam fvvcapdsal<br>181 rgharfspgr gvvvqhsast asmryslspg tpipeghtvd tafrtglpid evsffpfrsg<br>241 krmpaivsaf pqrgrvlcaf eerg |
| WP_041231581.1 (SEQ ID NO.32) | 1 mralarefgr ahaskdphal aeglgarlay mdlgerdgay dpehgvilvn gshsrerqrf<br>61 tlahevshal lladedllsd lhdtfdgeal enaietlcnv gaatilisdd dlrsalerfg<br>121 tsgqtiaeva rradvsapva lyaladfvrt pamfvvcapd salrgharfs pgrgvvvqhs<br>181 astasmrysl spgtpipegh tvdtafrtgl pidevsffpf rsgkrmpaiv safpqrgrvl<br>241 cafeerg |
| WP_034339224.1 (SEQ ID NO.33) | 1 mdpkpqhkar mrelaldfar thqardlysl geaagtklvf mdlgerdgay dpehkaiiin<br>61 ntrdlnrqkf tlaheiahal lldddddllsd ihedfegdsl eqvieklcdw gaaniliepe<br>121 tlqevlnrhg isaqgvmdls rkahislrsa mvaiaeqaqn ptlivlfqpa apqkplvvnf<br>181 taqnaafkyt ltpgqvlvqd hpvqvsfetr lpleedsyvp fasgkkmpah lttypekmrv<br>241 lavfktp |

It's well-known that IrrE protein coded by Dgeo0395 can specifically respond stress signals, and enhance expression of resistance genes of this bacterial strain own.

However, if s has not been reported yet that Dgeo0395 protein in *Deinococcus geothermalis* can enhance resistance against desiccation, oxidation and ultraviolet irradiation in other organisms. Also, the report that the key functional motif of this protein is analyzed, and its function thereof is optimized by site-specific mutagenesis has not been found yet.

SUMMARY OF THE INVENTION

The purpose of this invention is to modify the specific global regulatory protein IrrE of *Deinococcus* through gene engineering technology, to optimize the key functional motif of IrrE protein (Dgeo0395) of *Deinococcus geothermalis*, and obtain the sequence of new protein with better regulatory capacity, so as to enhance resistance of recombinant strain.

This invention analyses structural domains of regulatory protein Dgeo0395 through homology modeling. It's discovered that, Dgeo0395 consists of three domains, wherein, HTH domain plays a role of participate in combining target gene promoter. HTH domain consists of 3 α helix (α6, α7 and α8).

Wherein, α7 helix contains important domain motif "154LAELA159". Currently, all sequences of 23 homologous proteins of Dgeo0395 in NCBI database comprise this section of functional domain motif sequence, and this section of functional domain motif only be founded in *Deinococcus* strains (FIG. 1).

This invention analyses and compares the influences of amino-acid residues of different sites on stress resistance of whole regulatory protein Dgeo0395 by using site-specific mutagenesis of amino acids, and through stress resistance experiment results, find a mutation mode to perform amino acid optimization on the important functional domain motif 154LAELAR159 of regulatory protein Dgeo0395 of *Deinococcus geothermalis*.

The Specific Research Content is as Follows:

Amino-acid optimization on functional domain motif of Dgeo0395 gene

1). The functional analysis of structural domain is performed on amino acid sequence (as shown in SEQ ID NO. 2) of Dgeo0395 of *Deinococcus geothermalis*. And site-specific mutagenesis of amino acids is performed on the important functional motif 154LAELAR159 (as shown in SEQ ID NO. 3).

The following is amino acid sequence of Dgeo0395, wherein, the part with underline is functional domain motif 154LAELAR159.

MTQGQTPPEELSADPSPETGALAPAKARMRELATAYARRLPGLDTHSLMS

GLDATLTFMPMGDRDGAYDPEHRVVLINSRVRPERQRFTLAHEISHALLL

GDDDLLSDLHDAYEGERLEQVIETLCNVGAAAILMPETLIDELLARFGPS

GRA<u>LAELARR</u>ADVSASSALYALAERTSVPVLYAVCAVSRLEAESGEERLP

EKALTVRASAGSPGVKYSLRPGTLIPDDHPVAVALETRLPITQESYVPFR

SGRRMPAYVDAFPERQRVLVSFALLPKATKGGEQDESGV

Said site-specific mutagenesis is the 2$^{nd}$ site of alanine (155A) and/or the 5$^{th}$ site of alanine (158A) on the functional domain motif 154LAELAR159 are mutated to serine.

Wherein, the 2$^{nd}$ site of alanine (155A) on the functional domain motif 154LAELAR159 is mutated to serine, with the sequence shown as SEQ ID NO. 4; the 5$^{th}$ site of alanine is mutated to serine, with the sequence shown as SEQ ID NO. 5. If s shown as the following table:

tance against ultraviolet irradiation of the recombinant strain which expresses the optimized Dgeo0395 protein (Dgeo0395-A155S and Dgeo0395-A158S) is enhanced more than 10 times (see also example 3 and FIG. 4, 5).

3). Amino acid site-specific mutagenesis is performed on the same functional domain motif of homologous protein DR-0167 (as shown in SEQ ID NO. 6) and DGo_CA2805 (as shown in SEQ ID NO. 7), and the analysis of resistance against ultraviolet irradiation stress is performed.

It's demonstrated by this experiment that, the functional domain motif function and its modification referred in this invention apply to not only Dgeo0395 protein of *Deinococcus geothermalis*, but also multiple homologous proteins of Dgeo0395. s indicated that there is a generality in the effect of modification of this functional domain motif on resistance function of homologous proteins against ultraviolet irradiation stress.

Information of Sequence List

SEQ ID NO. 1: DNA sequence of Dgeo0395 gene; gene sequence of *Deinococcus geothermalis* IrrE, which is a natural sequence of wild type without any modification;

SEQ ID NO. 2: amino acid sequence of Dgeo0395; amino acid sequence of *Deinococcus geothermalis* IrrE (protein number Dgeo0395), which is a natural sequence without any modification, and has capacity to enhance resistance of host against oxidation;

SEQ ID NO.3: the functional domain motif 154LAELAR159 in *Deinococcus geothermalis* IrrE found by this invention;

SEQ ID NO.4: artificial modification on the functional domain motif shown as SEQ ID NO.3, the second site of A is changed to S;

SEQ ID NO.5: artificial modification on the functional domain motif shown as SEQ ID NO.3, the fifth site of A is changed to S;

SEQ ID NO. 6: amino acid sequence of *D. radiodurans* IrrE (protein number DR_0167), which is a natural sequence without any modification. This protein is a homologous protein of *Deinococcus geothermalis* Dgeo0395 of this invention. This invention has modified its similar functional domain motif, and obtained the same stress resistance effect.

SEQ ID NO. 7: amino acid sequence of *Deinococcus gobiensis* IrrE (protein number DGo_CA2805), which is a natural sequence without any modification. This protein is a homologous protein of *Deinococcus geothermalis*

TABLE 1 optimization of amino acid on the functional domain motif of Dgeo0395 gene

| SEQ ID NO. | sequence | Notes |
|---|---|---|
| 3 | Leu Ala Gln Leu Ala Arg | 154LAELAR159 |
| 4 | Leu Ser Gln Leu Ala Arg | the second site of alanine is mutated to serine |
| 5 | Leu Ala Glu Leu Ser Arg | the fifth site of alanine is mutated to serine |

2). The recombinant engineering strain with mutant gene is constructed, and resistance of recombinant strain against desiccation, oxidation and ultraviolet irradiation stress is identified It's demonstrated by this experiment that, the functional domain motif 154LAELAR159 is important for *Deinococcus geothermalis* to play the function of Dgeo0395. Comparing with recombinant strain before optimization, resis- Dgeo0395 of this invention, and also has capacity to enhance resistance of host against oxidation. This invention has modified the similar functional domain motif, and also verified the important function of this functional domain motif.

SEQ ID NO.8: the modified amino acid sequence of *Deinococcus geothermalis* IrrE. The functional domain motif 154LAELAR159 in this protein has been modified, the second site of A is changed to S, to make resistance of the natural protein against oxidation enhanced 10 times.

SEQ ID NO.9: the modified amino acid sequence of *Deinococcus geothermalis* IrrE. The functional domain motif 154LAELAR159 in this protein has been modified, the fifth site of A is changed to S, to make resistance of the natural protein against oxidation enhanced almost 1000 times.

SEQ ID NO.10: the modified amino acid sequence of *Deinococcus geothermalis* IrrE. The functional domain motif 154LAELAR159 in this protein has been modified, the second site of A is changed to S, the fifth site of A is changed to S.

DETAILED DESCRIPTION OF THE INVENTION

The plasmids and strains described in the following examples are just used for further explaining this invention, instead of limiting the substantive content or scope of the invention. Where no specific experimental conditions are indicated, all the conditions are according to conventional conditions well known to a person skilled in the art, such as, the conditions recorded in Sambrook et al., "Molecular Cloning: A Laboratory Manual" (New York: Cold Spring Harbor Laboratory Press, 1989), or according to the conditions recommended by manufacturers.

The sources of the plasmid and strains in examples are as follows:

Cloning vector pJET: commercially available products of ThermoFisher;

Shuttle plasmid pRADZ3: preserved in the applicant's laboratory;

*E. coli* JM 109: commercially available products of Beijing TransGen Biotech Company.

Embodiment 1. *Deinococcus geothermalis* Dgeo0395 Gene Sequence Expression in *E. coli*

I. Experimental Method

1. PCR specific primers were designed based on the published sequence of Dgeo0395 gene in the genome of *Deinococcus geothermalis* strain DSM 11300.

```
                                          (SEQ ID NO.34)
0395-F:
5' ACCACTAGT ATGACGCAGGGCCAGACCCC 3'

(SEQ ID NO.35)
0395-R:
5' ACCCATATG TCAGACACCCGACTCATCCT 3'
```

2. The target gene sequence was amplified from the genomic DNA of *Deinococcus geothermalis* strain DSM 11300 by PCR method.

Reaction conditions: 94° C. 10 min, [94° C. 30 sec, 60° C. 30 sec, 72° C. 1.5 min] 35 cycles, 72° C. 10 min.

3. PCR products were cloned on the vector pJET after gel extraction which was named as pJET-0395 and was confirmed by sequencing. Then, Dgeo0395 gene containing the cohesive end and pRADZ3 vector containing groEL promoter were obtained by SpeI/NdeI double enzymes digestion. Dgeo0395 gene was connected to pRADZ3 vector to construct *E. coli* expression vector pRADZ3-0395.

Figure 2:
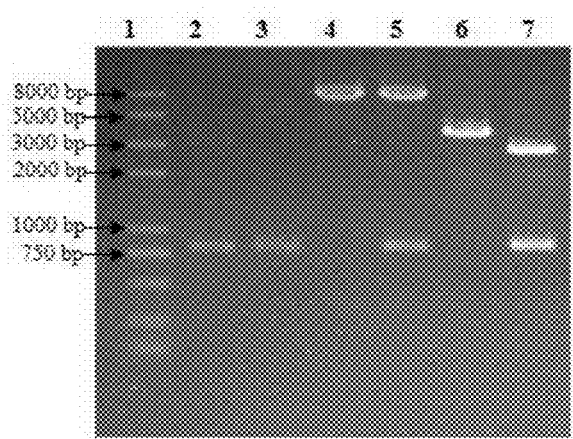
FIG. 2 is electrophoretogram of PCR product including sequence of *Deinococcus geothermalis* Dgeo0395 and vector verification;
Lane 1: 2K plus Marker; Lane 2~3: PCR product of pJET-0395; Lane 4: pRADZ3-0395/NdeI; Lane 5: pRADZ3-0395/NdeI+Spe I; Lane 6: pRADZ3-0395/Spe I; Lane 7: pRADZ3-0395/NdeI+Spe I

4. The expression vector was transformed into *E. coli* JM109. Whether the inserted sequence is inserted correctly was verified through PCR, enzyme digestion and sequencing (see also FIGS. 2, 3). This strain was named as JM-0395. *E. coli* JM109 containing pRADZ3 empty plasmid was named as JM-Z3.

II. Experimental Result

The recombinant *E. coli* engineering strain expressing Dgeo0395 was successfully constructed.

Embodiment 2. Stress Resistance Experiment of the Recombinant Engineering Strain Containing Dgeo0395 Gene of *Deinococcus geothermalis*

I. Experimental Material

The recombinant engineering strain: JM-0395 strain containing *Deinococcus geothermalis* strain Dgeo0395 obtained in example 1

Control strain: JM-Z3 strain containing the empty plasmid as described in example 1.

II. Experimental Method

1. The control strain and the recombinant engineering strain were activated by streaking on LB solid medium plates;
2. a single colony was picked to inoculate in liquid LB medium with the corresponding antibiotic and incubated at 37° C. into the mid and late exponential growth stages;
3. Thalli were collected by centrifugation at 6,000 rpm for 5 min at room temperature, then thalli were washed twice with the same volume of phosphate buffer (pH 7.0), and shocked evenly;

next, experiments of resistance against UV irradiation, mitomycin C and desiccation were performed.

A. UV Irradiation Resistance Analysis

1) The bacteria liquid was divided into two parts of equal volumes;
2) One part was centrifuged at 6,000 rpm for 5 min at room temperature to collect thalli as a control;
3) The other part of bacteria liquid was irradiated by UV for 5 min, and then thalli were collected after centrifugation at 6,000 rpm for 5 min at room temperature;
4) The bacteria liquid in different time was diluted 10 times to $10^{-5}$. 10 μL of bacteria liquid was pointed on LB solid culture medium plate, incubated at 37° C. for 2 d for observing, and recording the growth of different strains;
5) The bacteria liquid in different time was diluted 10 times to $10^{-5}$. 200 μL, of bacteria liquid was spread on LB solid culture plate and incubated at 37° C. for 2 d, the number of bacterial colony was recorded, the survival rate of the strain was calculated; this experiment was repeated 3 times.

B. Mitomycin C Oxidation Resistance Analysis

1) The bacteria liquid was divided into two parts of equal volumes;
2) One part was centrifuged at 6,000 rpm for 5 min at room temperature to collect thalli as a control;
3) The thalli were resuspended in LB liquid medium with mitomycin C at a final concentration of 10 μg/mL and shakily cultured at 30° C. and 220 rpm for 5 min, 10 min and 15 min;
4) The bacteria liquid in different time was diluted 10 times to $10^{-5}$. Taking 10 μL of diluted bacteria liquid and pointing on the LB solid culture medium plate, incubated at 37° C. for 2 d for observing and recording the growth of different strains;
5) The bacteria liquid in different time was diluted 10 times to $10^{-5}$. Taking 200४, of bacteria liquid was spread on LB solid culture plate, incubated at 37° C. for 2 d, the number of bacterial colonies was recorded, the survival rate of the strain was calculated, and this experiment was repeated 3 times.

C. Desiccation Shock Analysis

1) The bacteria liquid was divided into two parts of equal volumes;
2) One part was centrifuged at 6,000 rpm for 5 min at room temperature to collect thalli as a control;
3) The other part was packed in an open Eppendorf tube and placed in a sterile drier (granular silica gel was taken as a desiccant);
4) A batch of several different strains was taken out every 10 days, and multiple proportion diluted to $10^{-5}$, and then 104, was pointed on the LB solid culture medium plate, incubated at 37° C. for 2 d to observe, and record the growth of different strains;
5) The bacteria liquid in different time was diluted 10 times to $10^{-5}$. Taking 10 μL of diluted bacteria liquid and spread on LB solid culture plate and incubate at 37° C. for 2 d, the number of bacterial colonies was recorded, the survival rate of the strain was calculated, and this experiment was repeated 3 times.

III. Experimental Result

Figure 3:
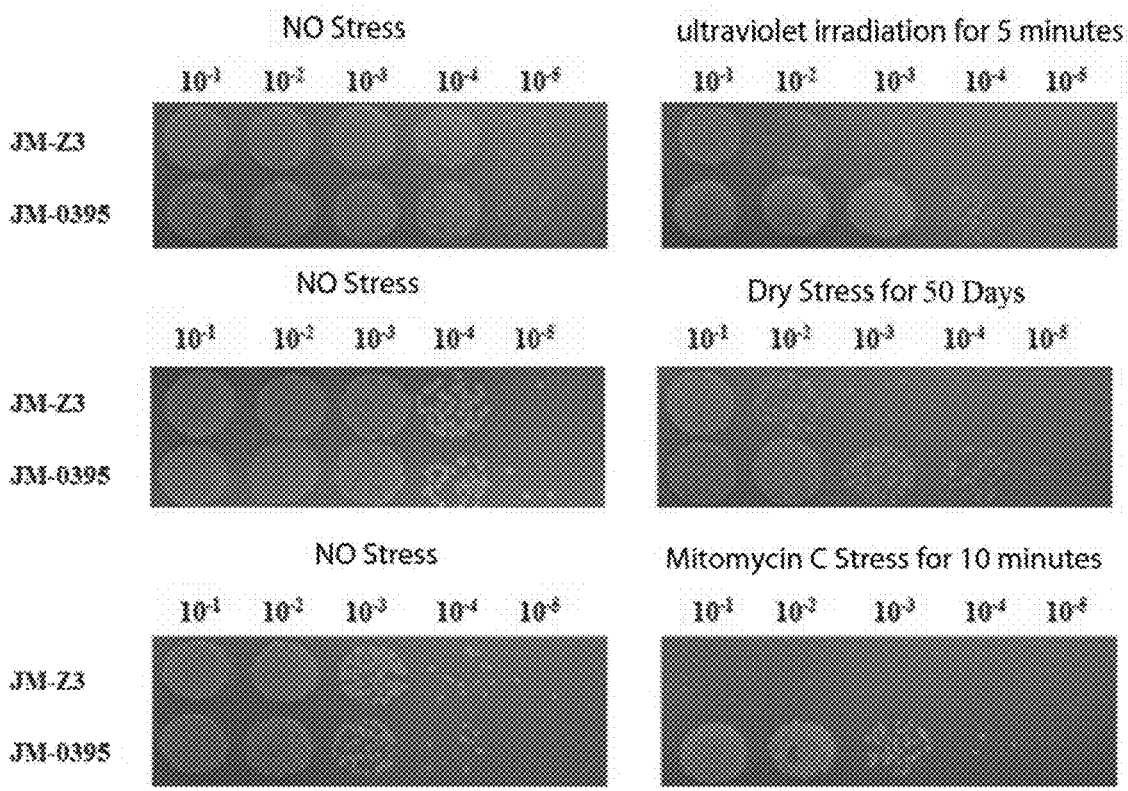
FIG. 3 is growth contrast between *Escherichia coli* with prokaryotic expression vector containing *Deinococcus geothermalis* Dgeo0395 (JM-0395) and *Escherichia coli* with empty vector (JM-Z3), before and after being subjected to stresses of ultraviolet irradiation, oxidation of mitomycin C and desiccation.

As shown in FIG. 3, the growth status of JM-0395 strain containing *Deinococcus geothermalis* strain Dgeo0395 was basically consistent with that of JM-Z3 strain containing empty plasmid before UV irradiation, mitomycin C and desiccation shock.

Figure 5:
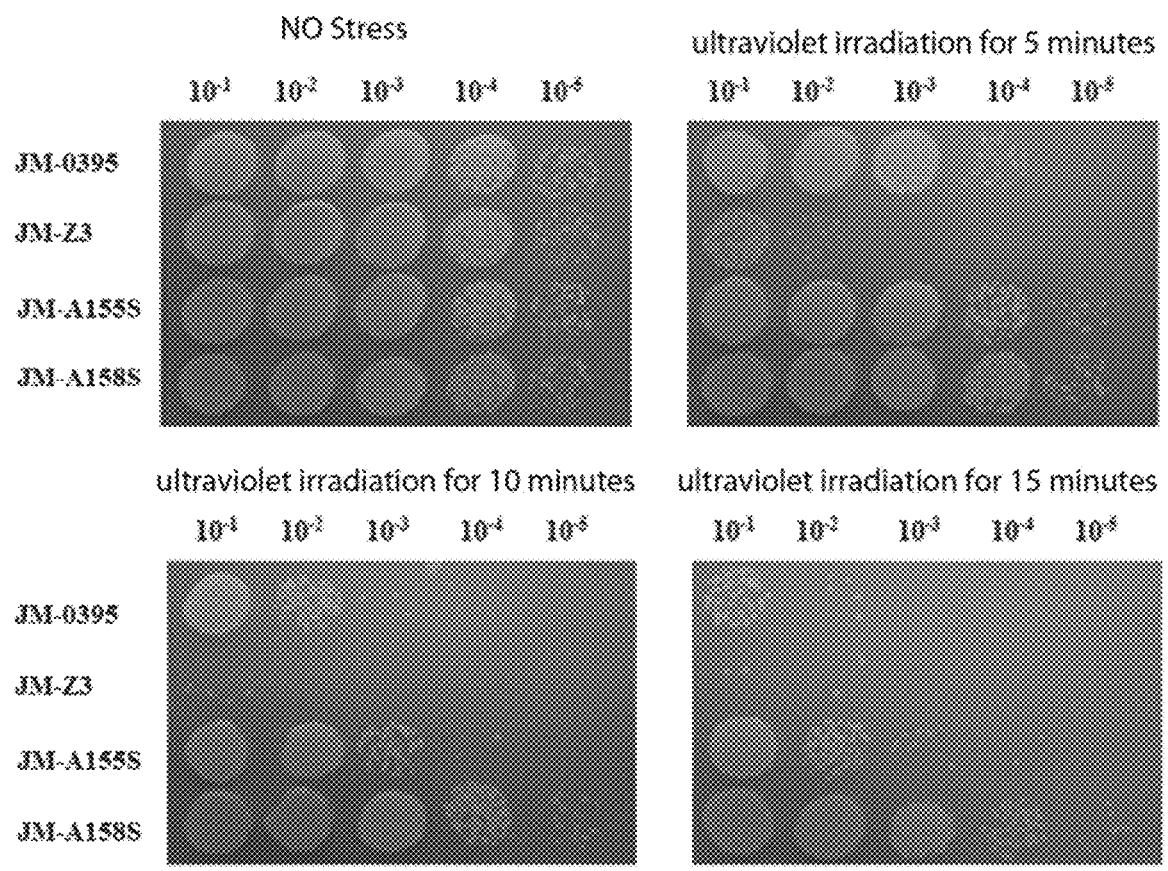
FIG. 5 is growth contrast between *Escherichia coli* with prokaryotic expression vector containing *Deinococcus geothermahs* Dgeo0395 (JM-0395) and strains JM-A155S as well as JM-A158S with mutant vector containing the functional domain motif, before and after being subjected to stresses of ultraviolet irradiation.

After UV irradiation, mitomycin C and desiccation shock, The JM-0395 recombinant strain containing *Deinococcus geothermalis* strain Dgeo0395 gene grew well, whose bacteria colony number was significantly higher than that of the JM-Z3 strain containing only the empty plasmid (see also FIG. 5). The UV irradiation resistance and desiccation stress resistance increased 2 orders of magnitude about 100 times than the control strain. Mitomycin C oxidative stress resistance increased 3 orders of magnitude, about 1000 times.

It's clearly found through the survival rate calculation of strain after the stress shock that:

After UV irradiation, the survival rate of the control strain was 0.644%±0.052%, and the survival rate of the JM-0395 strain expressing strain Dgeo0395 was 45.570%±3.797%, which was nearly 70 times higher than the control strain.

After desiccation stress treatment, the survival rate of the control strain was 3.040%±0.929%, while the survival rate of JM-0395 strain was 88.889%±7.274%, which was nearly 30 times higher than the control strain.

After the mitomycin C oxidative stress, almost all of the control strains were dead, while the survival rate of JM-0395 strain was 58.642%±4.660%, and the viability of JM-0395 strain was significantly higher than the control strain.

Table 2 shows comparison between the survival rates of the strain containing the empty vector (JM-Z3) and the recombinant *E. coli* strain (JM-0395) containing *Deinococcus geothermalis* Dgeo0395 gene before and after stress treatments of UV irradiation, mitomycin C oxidation and desiccation.

TABLE 2

Comparison of the strains survival rates after three stress treatment

| Stress treatment | Control strains JM-Z3 | Experimental strains JM-0395 | The times of Experimental strains on the improved survival status |
|---|---|---|---|
| UV irradiation | 0.644% ± 0.052% | 45.570% ± 3.797% | About 70 |
| Desiccation | 3.040% ± 0.929% | 88.889% ± 7.274% | About 30 |
| Mitomycin C oxidation | Almost all dead | 58.642% ± 4.660% | N/A |

IV. Experimental Conclusion

*Deinococcus geothermalis* strain Dgeo0395 gene significantly increased the ability of prokaryotes against stresses of UV irradiation, oxidation and desiccation.

Embodiment 3. Construction of the Amino Acid Optimization Sequence of the Functional Domain Motif of *Deinococcus geothermalis* Dgeo0395 Gene Based on the analysis data of the homologous gene sequence alignment, amino acid sequence of the important functional domain motif 154LAELAR159 of *Deinococcus geothermalis* Dgeo0395 expression protein was optimized.

I. Experimental Method

Figure 1:
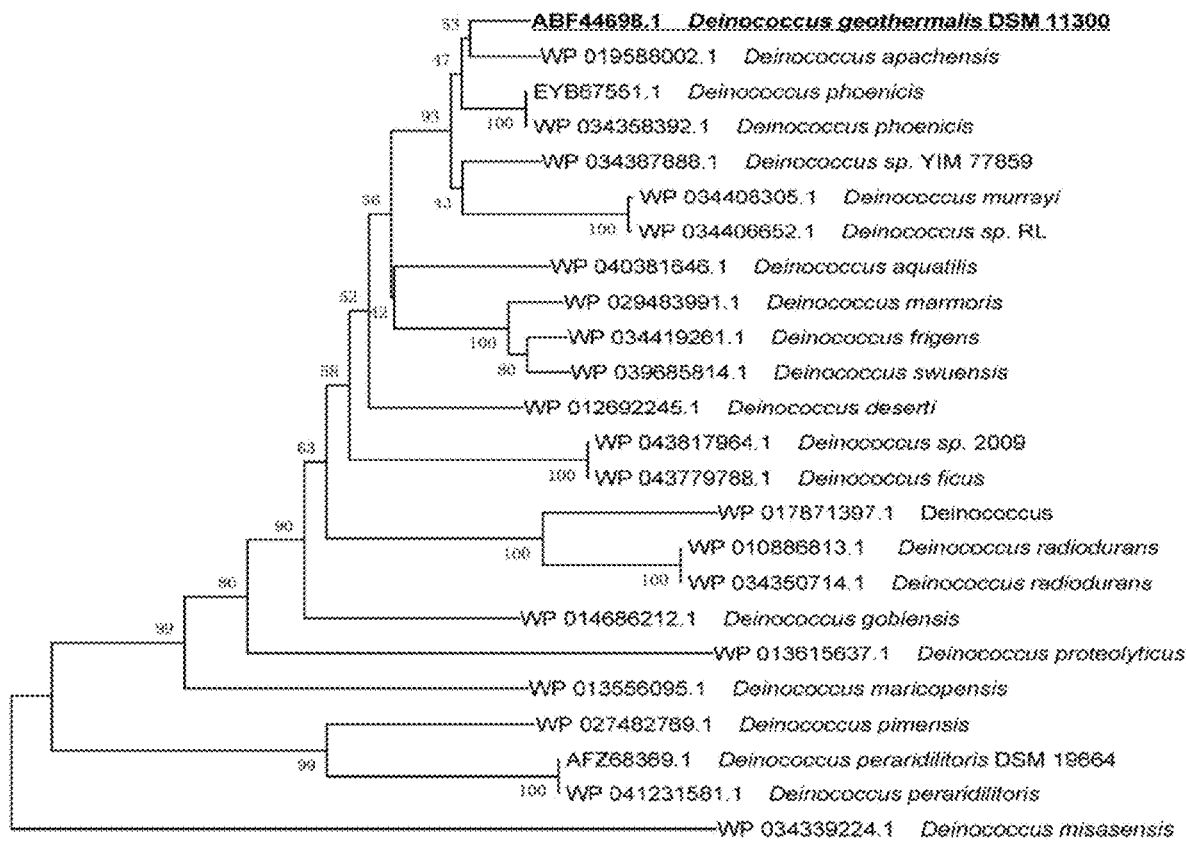
FIG. 1 is a phylogenetic tree of Dego0395 and its homologous proteins. One marked by transverse line is Dgeo0395 protein, protein sequence in this figure comprises all currently found homologous proteins of Dgeo0395, in total 23 homologous proteins. Data is from NCBI (the US National Center for Biotechnology Information) database.

Amino acid optimization was conducted for the important functional motif 154LAELAR159 of *Deinococcus geothermalis* regulatory protein Dgeo0395. The domain of the regulatory protein Dgeo0395 was analyzed by homology modeling. The Dgeo0395 consists of three domains, wherein the HTH domain participated in target gene promoter binding. The HTH domain consists of three a helixes (α6, α7 and α8), wherein the α7 helix contains an important functional domain motif 154LAELA159. Currently, in total 23 sequences of the Dgeo0395 homologous protein are found in the NCBI database, and are found only in the *Deinococcus* strain (FIG. 1). These protein sequences all contain this functional domain motif. By using the method of amino acid site-directed mutagenesis, the effect of amino acid residues at different sites on resistance against stresses of the whole regulatory protein Dago0395 was analyzed.

1. The optimization analysis of the amino acid sequence of the functional domain motif 154LAELAR159 of *Deinococcus geothermalis* Dgeo0395 was performed by amino acid site-directed mutagenesis. Nucleotide sequence of encoding amino acid of target site was mutated by fusion PCR method, and protein mutant of changing site mutation was obtained. The selected mutation sites were 154L, 155A, 157L, 158A and 159R. Respectively the 154th site of leucine was mutated to valine, the 155th site of alanine was mutated to serine, the 157th site of leucine was mutated to valine, the 158th site of alanine was mutated to serine, and the 159th site of arginine was mutated to lysine.

The primer sequences are as follows:

```
                                          (SEQ ID NO.34)
a-0395-F;
5' accactagtatgacgcagggccagacc 3'

(SEQ ID NO.35)
d-0395-R:
5' acccatatgtcagacacccgactcatcct 3'

(SEQ ID NO.36)
b1-L154V-F:
5' gggcgtgcgGTGgctgagctggcgcggcgggcagacgtga 3'

(SEQ ID NO.37)
c1-L154V-R:
5' tcacgtctgcccgccgcgccagctcagcCACcgcacgccc 3'

(SEQ ID NO.38)
b2-A155S-F:
5' gggcgtgcgctgAGCgagctggcgcggcgggcagacgtga 3'

(SEQ ID NO.39)
c2-A155S-R:
5' tcacatctgcccgccgcgccagctcGCTcaccgcacgccc 3'

(SEQ ID NO.40)
b3-L157V-F:
5' gggcgtgcgctggctgagGTGgcgcggcgggcagacgtga 3'

(SEQ ID NO.41)
c3-L157V-R:
5' tcacgtctcccgccgcgccagCACagccaccgcacgccc 3'

(SEQ ID NO.42)
b4-A158S-F:
5' gggcgtgcgctggctgagctgAGCcggcgggcagacgtga 3'

(SEQ ID NO.43)
c4-A158S-R:
5' tcacgtctgcccgcccGCTcagctcagccaccgcacgccc 3'

(SEQ ID NO.44)
b5-R159K-F
5' gggcgtgcgctggctgagaggcgAAgcgggcagacgtga 3'

(SEQ ID NO.45)
c5-R159K-R:
5' tcacgtctgcccgCTTcgccagctcagccacgcacgccc 3'
```

2. Two primers b and c containing the site-directed mutagenesis sequences were designed at the nucleic acid sites to be mutated, meanwhile the upstream and downstream primers a and d of the gene were designed. Two fragments 1 and 2 were obtained by PCR amplification respectively using the primers a, b and c, d by taking the genome as template. Afterwards the two fragments 1, 2 were mixed at a molar ratio of 1:1, and the mixture was taken as a template, and these two fragments were fused by using the primers a and d.

The reaction conditions of fragment 1, 2: 94° C. 10 min, [94° C. 30 sec, 60° C. 30 sec, 72° C. 1.5 min] 30 cycles, 72° C. 10 min.

Fusion reaction conditions: 94° C. 10 min, [94° C. 30 sec, 60° C. 30 sec, 72° C. 2 min] 40 cycles, 72° C. 10 min.

3. The recombinant engineering strains JM-L154V, JM-A155S, JM-L157V, JM-A158S-F, JM-R159K were obtained by link the obtained recombinant mutant fragment to vector pRADZ3 and transformed into *E. coli* (method referred to example 1).

II. Experimental Result

The recombinant engineering strains JM-L154V, JM-A155 S, JM-L157V, JM-A158S-F, JM-R159K which express the amino acid mutant sites on the important functional domain motif 154LAELAR159 of *Deinococcus geothermalis* regulatory protein Dgeo0395 were successfully constructed.

Embodiment 4. The Stress Resistance Experiment of the Optimized Recombinant Engineering Strain Expressing Important Functional Domain Motif 154LAELAR159 of *Deinococcus geothermalis* Strain Dgeo0395 Protein

I. Experimental Purpose

It aims to indentify resistance of each recombinant strain against stresses of desiccation, oxidation and UV irradiation, and to compare with the blank control and the original strains.

II. Experimental Material

The recombinant engineering strain: the recombinant engineering strain JM-L154V, JM-A155S, JM-L157V, JM-A158S-F, JM-R159K expressing the amino acid mutant sites on the importantly functional domain motif 154LAELAR159 of *Deinococcus geothermalis* regulatory protein Dgeo0395 obtained by example 3.

Control Strain:

Said JM-Z3 strain containing empty plasmid of example 1; Said the JM-0395 strain containing *Deinococcus geothermalis* strain Dgeo0395 of example 1.

III. Experimental Method

Experiments for the resistance of each strain against three stresses of desiccation, oxidation and UV irradiation was carried on according to the experimental method of example 2.

IV. Experimental Results

1. UV Stress

The results are shown in the following table

TABLE 2

Comparison on survival rates between each strain under UV irradiation stress

| Experimental strain | | Survival rates (%) | | | |
|---|---|---|---|---|---|
| Name | Remarks | 0 Min | 5 Min | 10 Min | 15 Min |
| JM-Z3 | Negative control strain | 100 | 0.052 | No strain survival | No strain survival |
| JM-0395 | Unmodified bacteria 154LAELAR159 (SEQ ID NO.3) | 100 | 5.682 | 0.125 | 0.014 |
| JM-L154V | modified bacteria 1 154VAELAR159 (SEQ ID NO.56) | 100 | 6.364 | 0.159 | 0.009 |
| JM-A155S | modified bacteria 2 154LSELAR159 (SEQ ID NO.4) | 100 | 44.737 | 1.263 | 0.197 |
| JM-L157V | modified bacteria 3 154LAEVAR159 (SEQ ID NO.57) | 100 | 4.545 | 0.147 | 0.018 |
| JM-A158S | modified bacteria 4 154LAELSR159 (SEQ ID NO.5) | 100 | 75.000 | 62.500 | 11.750 |
| JM-R159K | modified bacteria 5 154LAELAK159 (SEQ ID NO.58) | 100 | 3.636 | 0.141 | 0.023 |

When UV stress treating for 10 min, the control strain JM-Z3 had all died, and the survival rate of the recombinant strain JM-0395 expressing *Deinococcus geothermalis* Dgeo0395 was reduced to 0.125%. However, the survival rate of the recombinant strain JM-A155S expressing the Dgeo0395 optimized gene was 1.263%, and the survival rate of the recombinant strain JM-A158S expressing Dgeo0395 optimized gene was the best, keeping at 62.5%.

The mutation sites of each modified bacteria were:

JM-L154V: the 154$^{th}$ site of leucine mutation to valine;

JM-A155S: the 155$^{th}$ site of alanine mutated to serine, i.e., amino acid sequences as shown in SEQ, ID, NO. 4;

JM-L157V: the 157$^{th}$ site of leucine mutation to valine;

JM-A158S: the 158$^{th}$ site of alanine mutation to serine;

JM-R159K: the 159$^{th}$ site of arginine mutation to lysine, i.e., amino acid sequences as shown in SEQ, ID, NO. 5;

When UV stress treating for 15 min, the survival rate of the recombinant strain JM-0395 expressing *Deinococcus geothermalis* Dgeo0395 was further reduced to 0.014%. However, the survival rate of the recombinant strain JM-A155S expressing the Dgeo0395 optimized gene was 0.197%, and the survival rate of the recombinant strain JM-A158S expressing Dgeo0395 optimized gene remained at around 12% (Table 2).

Figure 6:
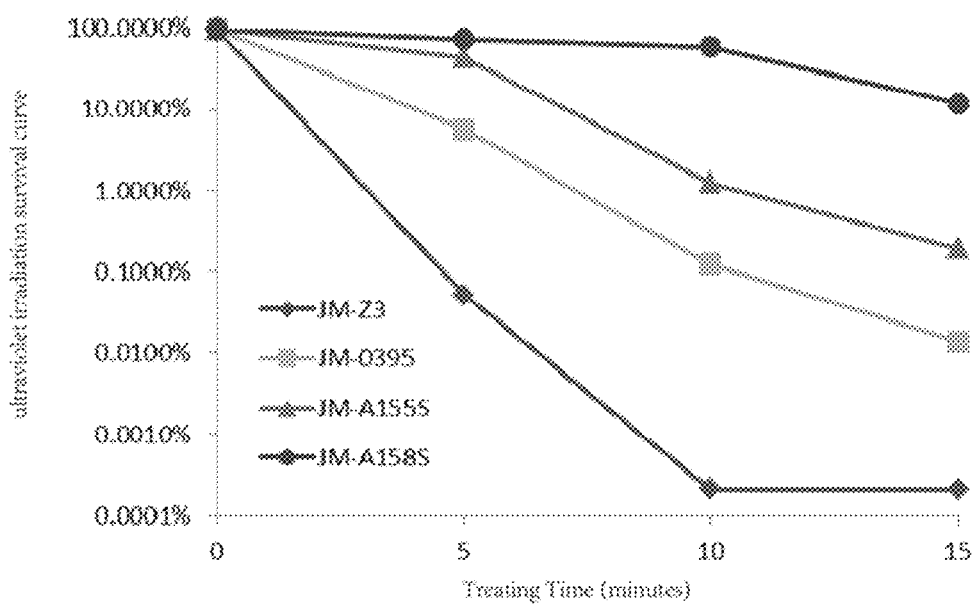
FIG. 6 is survival curve of *Escherichia coli* with prokaryotic expression vector containing *Deinococcus geothermahs* Dgeo0395 (JM-0395) and strains JM-A155S as well as JM-A158S with mutant vector containing the functional domain motif, before and after being subjected to stresses of ultraviolet irradiation.

It's shown by UV irradiation survival curve that, the modified protein expressed by the recombinant strain JM-A158S, whose amino acid sequence is shown in SEQ ID NO.8, and the 155$^{th}$ site of alanine in the functional domain motif 154LAELAR159 is mutated to serine, as shown in SEQ ID NO. 4, made the survival rate of the recombinant strain about 15 times higher than pre-mutation under irradiation for 15 min. However, the modified protein expressed by the recombinant strain JM-A155S, whose amino acid sequence is shown in SEQ ID NO.9, and the 158$^{th}$ site of alanine in the functional domain motif 154LAELAR159 is mutated to serine, as shown in SEQ ID NO. 5, made the survival rate of the recombinant strain about 900 times higher than pre-mutation under irradiation for 15 min (Table 2, FIG. 6).

Figure 4:
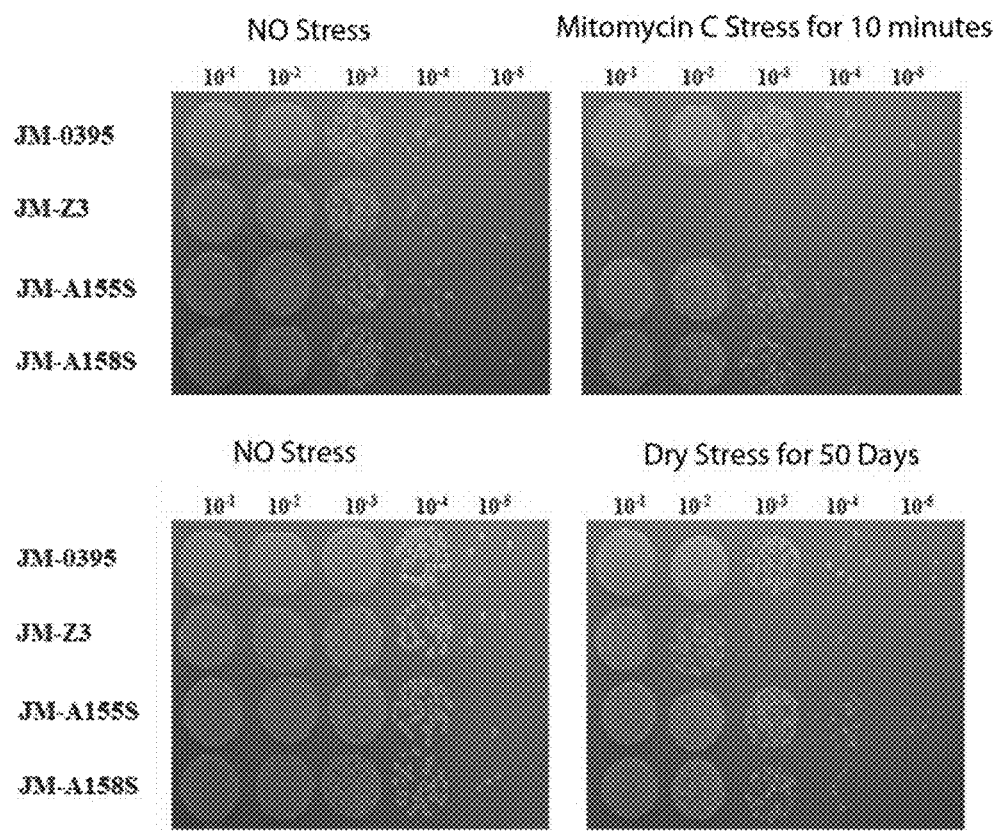
FIG. 4 is growth contrast between *Escherichia coli* with prokaryotic expression vector containing *Deinococcus geothermahs* Dgeo0395 (JM-0395) and strains JM-A155S as well as JM-A158S with mutant vector containing the functional domain motif, before and after being subjected to stresses of oxidation of mitomycin C and desiccation.

2. Resistance of the recombinant strain JM-A155S and JM-A158S against stresses of desiccation and oxidation Resistance of the recombinant strains JM-A155S and JM-A158S against stresses of desiccation and oxidation were consistent with the recombinant strain JM-0395 of pre-mutation (see also FIG. 4).

V. Experimental Conclusion

1. Resistance of the recombinant strain JM-A155S and JM-A158S with optimized functional domain motif against UV irradiation stress was significantly higher than the original strain JM-0395, which increased more than 10 times (FIG. 5).

Therefore, the 155$^{th}$ site and the 158$^{th}$ site of alanine in 154LAELAR159 were the active sites for enhancing anti-ultraviolet radiation stress function.

2. Resistance of the recombinant strains JM-L154V, JM-L157V and JM-R159K against desiccation, oxidation and ultraviolet irradiation were consistent with that of strain JM-0395, which were all higher than empty plasmid strains. It was demonstrated that the L154V, L157V and R159K site mutations on 154LAELAR159 did not affect resistance activity of the original bacteria, ie, no effect on the regulation of Dgeo0395.

3. The functional domain motif 154LAELAR159 of *Deinococcus geothermalis* Dgeo0395 had an important role in improving the resistance of the protein Dgeo0395.

Figure 7:
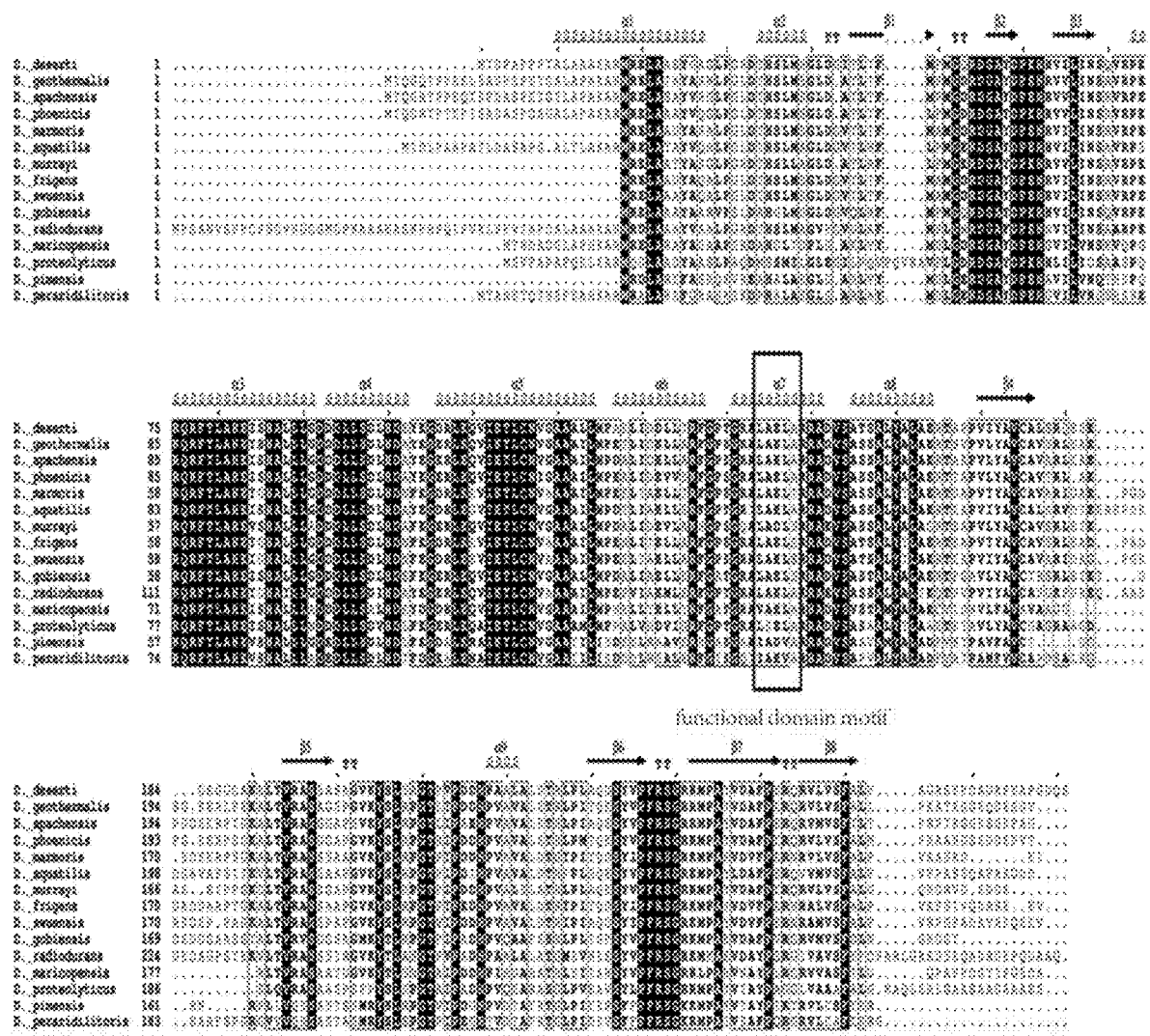
FIG. 7 is sequence alignment and structure analysis of Dego0395 and its homologous proteins thereof. The frame area is the functional domain motif referred by this invention. Protein sequence in this figure comprises all currently found homologous proteins of Dgeo0395, in total 15 homologous proteins. Data is from NCBI (the US National Center for Biotechnology Information) database. The sequences used for analysis are as follows: *D. deserti* (SEQ ID NO.21), *D. geothermalis* (SEQ ID NO.2), *D. apachensis* (SEQ ID NO.11), *D. phoenicis* (SEQ ID NO.12), *D. marmoris* (SEQ ID NO.18), *D. aquatilis* (SEQ ID NO.17), *D. murrayi* (SEQ ID NO.15), *D. frigens* (SEQ ID NO.19), *D. swuensis* (SEQ ID NO.20), *D. gobiensis* (SEQ ID NO.7), *D. radiodurans* (SEQ ID NO.6), *D. maricopensis* (SEQ ID NO.29), *D. proteolyticus* (SEQ ID NO.28), *D. pimensis* (SEQ ID NO.30), *D. peraridilitoris* (SEQ ID NO.31).

Embodiment 5 Modification of Amino Acid Sequence Optimization on the Functional Domain Motif of IrrE Homologous Protein in *Deinococcus Radiodurans* and UV Resistance Experiment I. Experimental Purpose Alignment analysis was performed on Dgeo0395 homologous protein sequence by using NCBI database gene information (see also FIGS. 1, 7). The homologous protein of Dgeo0395 in *Deinococcus radiodurans* was DR0167, which also contained the important functional domain motif 180LAELAR185 found by this invention in the α7 position, and the amino acid sequence was the same as Dgeo0395 (see also FIG. 7). The second or fifth site of alanine in the important functional domain motif 1801LAELAR185 of the homologous protein DR0167 in *Deinococcus radiodurans* was optimized, mutated and modified, to identify the role of the functional domain motif in resistance of the recombinant mutant protein against UV stress.

II. Experimental Method

1. The functional domain motif 180LAELAR185 with spatial structure of the same location on the amino acid sequence of the *Deinococcus radiodurans* IrrE homologous protein DR0167 was optimized and analyzed through amino acid site-directed mutagenesis manners. In the same way, the nucleotide sequence encoding the amino acid at target site was mutated by fusion PCR, in order to obtain protein mutant with site mutations. The selected mutation sites were two alanines of 181A and 184A in the functional domain motif. Respectively, the 181' site of alanine was mutated to serine, and the 184$^{th}$ site of alanine was mutated to serine.

The primer sequences were as follows:

(SEQ ID NO.46)
a-dr0167-F:
5' taactagtgtgcctagtgccaacgtcag 3'

(SEQ ID NO.47)
d-dr0167-R:
5' tacatagtcactgtgcagcgtcct 3'

(SEQ ID NO.48)
b1-A181S-F:
5' ggccccaccgggcgcgccctcAGCgaactcgccaagcgggc 3'

(SEQ ID NO.49)
c1-A181S-R:
5' ggcccgcttggcgagttcGCTgaggacacgcccggtggggcc 3'

(SEQ ID NO.50)
b2-A184S-F:
5' ggcccaccgggcgcgccctcgccgaactcAGCaagcgggcc 3'

(SEQ ID NO.51)
c2-A184S-R:
5' ggcccgcttGCTgagttcggcgagggcgcgcccggtggggcc 3'

2. The original gene fragment and the recombinant mutant fragment of the *Deinococcus radiodurans* DR0167 was connected to the vector pRADZ3 and transformed into *E. coli* (method referred to examples 1, 3). The recombinant engineering strains JM-DR0167, JM-A181S and JM-A184S were obtained.

3. The resistance experiment of each strain to UV irradiation was carried out according to the experimental method of example 2.

III. Experimental Result

Figure 8:
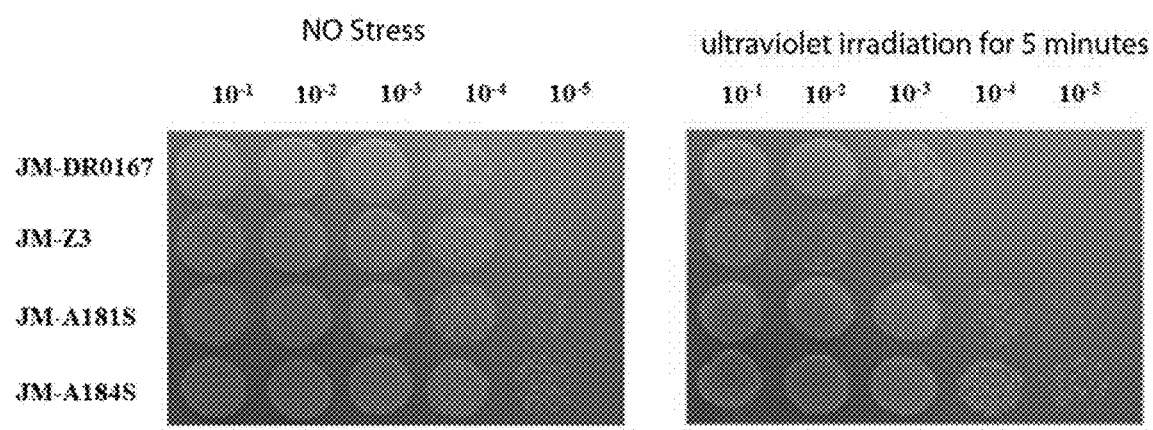
FIG. 8 is growth contrast between *Escherichia coli* expressing *D. radiodurans* DR-0167 (JM-DR0167) and strains JM-A155S as well as JM-A158S expressing protein with the mutant functional domain motif, before and after being subjected to stresses of ultraviolet irradiation.

It's shown by UV irradiation stress treatment that, *Deinococcus radiodurans* DR-0167 also could improve the prokaryotic microbial UV stress resistance. Similarly, that the second or fifth site of alanine on the functional domain motif 180LAELAR185 are optimized and mutated to serine can further enhance the ability of recombinant proteins to improve resistance of cell against UV irradiation (FIG. 8). It's shown by experiment results that, that the second site of alanine on the functional domain motif 180LAELAR185 is mutated to serine can increase only 10-fold on the protective effect compared with that of the original DR-0167 protein. However, that the fifth site of alanine on the functional domain motif 180LAELAR185 is mutated to serine can increase 2 orders of magnitude on the protective effect compared with the original DR-0167 protein, nearly enhancing at 100 times (see also FIG. 8).

IV. Experimental Conclusion

*Deinococcus radiodurans* DR-0167 was the homologous protein of Dgeo0395. DR-0167 also contains the important functional domain motif 180LAELAR185 found by this invention, whose amino acid sequence was the same as Dgeo0395. Its shown by the experimental results that, that the second or fifth site of alanine on the functional domain motif 180LAELAR185 was optimized and mutated to serine can further enhance the ability of the recombinant protein to enhance resistance of cell against anti-ultraviolet irradiation. It's shown by the experimental results that, the discovery mentioned in this invention that the second or fifth site of alanine on the important functional domain of the Dgeo0395 mentioned in this invention was mutated to serine, which can enhance this protein to protect resistance of prokaryotic cells against UV stress also applies to modification on resistance of Dgeo0395 homologous proteins against stress.

Embodiment 6 Modification on Amino Acid Sequence of the Functional Domain Motif of IrrE Homologous Protein in Deinococcus Gobiensis and UV Resistance Experiment Identification I. Experimental Purpose Dgeo0395 homologous protein sequence was analyzed through alignment by using NCBI database gene information (see also FIG. 1, 7). The homologous protein of Dgeo0395 in *Deinococcus* gobiensis is DGo_CA2805, which also contains the important functional domain motif 127LAELSR132 found by the invention on the α7 location, and its amino acid sequence is different from Dgeo0395, whose the fifth site was not alanine, but serine (see also FIG. 7). The fifth site of serine on the important functional domain motifs 127LAELSR132 of the homologous protein DGo_CA2805 in *Deinococcus* gobiensis was reversely mutated to alanine, to indentify the role of the functional domain motif in resistance of recombinant mutant protein against UV.

II. Experimental Method

1. The functional domain motif 127LAELSR132 with spatial structure of the same location on the amino acid sequence of the *Deinococcus* gobiensis IrrE homologous protein DGo_CA2805 was analyzed through amino acid site-directed mutagenesis manners. In the same way, the nucleotide sequence encoding the amino acid at target site was mutated by fusion PCR, in order to obtain protein mutant with site mutations. The selected mutation site was the fifth site of serine in the functional domain motif. The 131' site of serine was reversely mutated to alanine.

The primer sequences were as follows:

```
                                              (SEQ ID NO.52)
a-CA2805-F:
5' taactagtataggcgagctggcggcgg 3'

(SEQ ID NO.53)
d-CA2805-R:
5' tacatatgtgagagggagacgcgct 3'

(SEQ ID NO.54)
b1-S131A-F:
5' cgcgccctggccgagttgGCCcgccgcgccgacgtgagt 3'

(SEQ ID NO.55)
c1-S131A-R:
5' actcacgtcggcgcggcgGGCcaactcggccaggggcgcg 3'
```

2. The obtained original gene fragment and recombinant mutant fragment of *Deinococcus* gobiensis DGo_CA2805 were respectively connected to the vector pRADZ3 and transformed into *E. coli* (methods referred to examples 1, 3). The recombinant engineering strains JM-CA2805 and JM-S131A were obtained.

3. The resistance experiments of each strain against UV irradiation were carried out according to the experimental method of example 2.

III. Experimental Result

Figure 9:
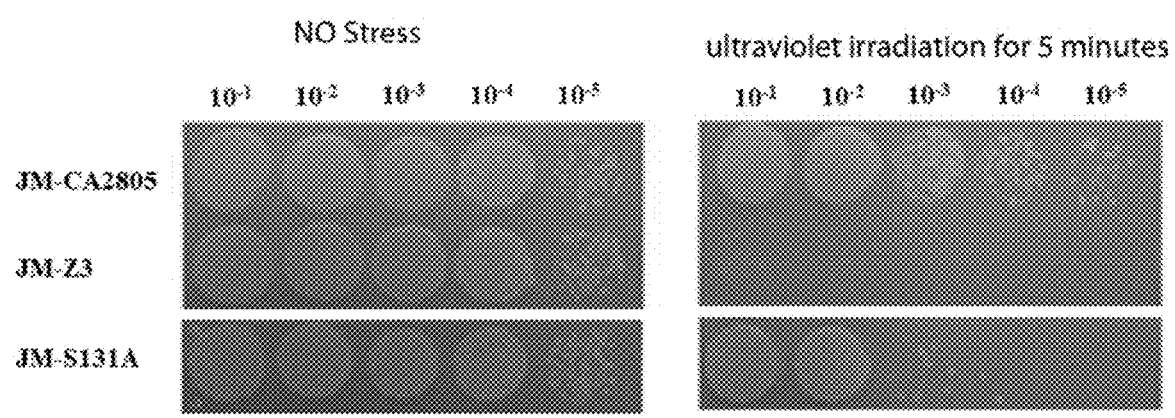
FIG. 9 is growth contrast between *Escherichia coli* expressing *Deinococcus* gobiensis DGO-CA2805 (JM-CA2805) and strain JM-5131A expressing protein with the mutant functional domain motif, before and after being subjected to stresses of ultraviolet irradiation.

It's shown by UV irradiation stress treatment that, *Deinococcus* gobiensis DGo_CA2805 also could improve resistance of the prokaryotic microbial against UV stress. Similarly, the fifth site of serine on the functional domain motif 127LAELSR132 was mutated to alanine, which significantly reduced the ability of recombinant proteins to improve cell resistance against UV irradiation (FIG. 9). It's shown by the experiment results that, that the fifth site of serine was mutated to alanine of the functional domain motif 127LAELSR132 reduced 2 orders of magnitude on the protective function of the original protein DGo_CA2805, nearly 100 times (see also FIG. 9).

IV. Experimental Conclusion

*Deinococcus* gobiensis DGo_CA2805 is the homologous protein of Dgeo0395. DGo_CA2805 also contains the important functional domain motif 127LAELSR132 found by this invention. Its amino acid sequence is different from Dgeo0395 and its fifth site of amino acid is natural serine. In this example, the amino acid at this site was reversely mutated, and the role of the functional domain motif in UV resistance function of the recombinant mutant protein was validated. It's shown by experimental results that, that the fifth site of serine mutation in the functional domain motif 127LAELSR132 was reversely mutated to alanine significantly reduced the ability of the recombinant protein to enhance cell resistance against anti-ultraviolet irradiation. It's proven by the experimental results from the opposite direction that, the discovery that the second or fifth site of alanine in the important functional domain of Dgeo0395 mentioned in the present invention is mutated to serine, which improves the ability of this protein to protect the resistance of prokaryotic cells against UV stress also applies to modification on resistance of Dgeo0395 homologous proteins against stress.

We claim:

1. A method of enhancing stress resistance of *E. coli*, comprising following steps:

performing amino acid optimization on a functional domain motif LAELAR (SEQ ID NO: 3) of *Deinococcus geothermalis* IrrE protein, wherein the amino acid optimization is the 2$^{nd}$ site alanine or the 5$^{th}$ site alanine on the functional domain motif LAELAR being mutated to a serine;

constructing an expression vector containing a nucleotide sequence encoding optimized protein of said IrrE protein;

transforming said expression vector into *E. coli* cells;

subjecting the *E. coli* cells containing said expression vector to oxidation, ultraviolet irradiation or desiccation stress, and selecting the *E. coli* cells for improved stress resistance.

2. The method according to claim 1, wherein the stress resistance is a resistance against the ultraviolet irradiation stress.

3. The method according to claim 1, wherein the *Deinococcus geothermalis* IrrE protein is Dgeo0395 protein comprising the amino acid sequence set forth in SEQ ID NO: 2.

* * * * *